(12) United States Patent
Benito et al.

(10) Patent No.: US 8,143,397 B2
(45) Date of Patent: Mar. 27, 2012

(54) PROCESS FOR PREPARING VORICONAZOLE, NEW POLYMORPHIC FORM OF INTERMEDIATE THEREOF, AND USES THEREOF

(75) Inventors: Monica Benito, L'hospitalet De Llobregat (ES); Elies Molins, Sant Feliu De Llobregat (ES); Juan Contreras, Celra (ES)

(73) Assignee: Medichem S.A., Barcelona (ES)

( * ) Notice: Subject to any disclaimer, the term of this patent is extended or adjusted under 35 U.S.C. 154(b) by 836 days.

(21) Appl. No.: 12/278,030

(22) PCT Filed: Jan. 29, 2007

(86) PCT No.: PCT/IB2007/002173
§ 371 (c)(1),
(2), (4) Date: Aug. 1, 2008

(87) PCT Pub. No.: WO2007/132354
PCT Pub. Date: Nov. 22, 2007

(65) Prior Publication Data
US 2009/0023922 A1    Jan. 22, 2009

Related U.S. Application Data

(60) Provisional application No. 60/806,666, filed on Jul. 6, 2006, provisional application No. 60/764,057, filed on Feb. 1, 2006.

(51) Int. Cl.
*C07D 403/10* (2006.01)
(52) U.S. Cl. ........................................ 544/333
(58) Field of Classification Search .................. 544/333
See application file for complete search history.

(56) References Cited

U.S. PATENT DOCUMENTS

| | | | |
|---|---|---|---|
| 567,817 | A | 9/1896 | Snyder |
| 5,567,817 | A | 10/1996 | Ray et al. |
| 6,586,594 | B1 * | 7/2003 | Butters et al. ............. 544/333 |

FOREIGN PATENT DOCUMENTS

| | | | |
|---|---|---|---|
| CN | 1488629 | * | 4/2004 |
| EP | 1 157 726 | | 11/2001 |
| WO | WO 97/06160 | | 2/1997 |
| WO | WO 2006/065726 | | 6/2006 |
| WO | WO 2007/013096 | | 2/2007 |

OTHER PUBLICATIONS

Mike Butters, et al., Process Development of Voriconazole: A Novel Broad-Spectrum Triazole Antifungal Agent, Organic Process Research & Development (2001) vol. 5, p. 28-36.

* cited by examiner

*Primary Examiner* — Venkataraman Balasubramanian
(74) *Attorney, Agent, or Firm* — Frommer Lawrence & Haug LLP

(57) ABSTRACT

The present invention relates to an improved process for preparation of Voriconazole and Voriconazole (1R)-(−)-10-camphorsulfonate.

14 Claims, 9 Drawing Sheets

PROCESS FOR PREPARING VORICONAZOLE, NEW POLYMORPHIC FORM OF INTERMEDIATE THEREOF, AND USES THEREOF

RELATED APPLICATIONS/INCORPORATION BY REFERENCE

This application claims priority to U.S. Provisional Application No. 60/806,666, filed on 6 Jul. 2006 and 60/764,057, filed on 1 Feb. 2006.

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

FIELD OF THE INVENTION

The present invention relates to an improved process for the preparation of Voriconazole and a new polymorphic form of Voriconazole (1R)-(−)-10-camphorsulfonate.

BACKGROUND OF THE INVENTION

Voriconazole is a commercially marketed pharmaceutically active substance known to be useful for the treatment of some fungal infections. Voriconazole has an empirical formula of $C_{16}H_{14}F_3N_5O$ and a molecular weight of 349.3. Voriconazole is the international common accepted name for (2R,3S)-2-(2,4-difluorophenyl)-3-(5-fluoropyrimidin-4-yl)-1-(1H-1,2,4-triazol-1-yl)butan-2-ol, which is represented in formula (I).

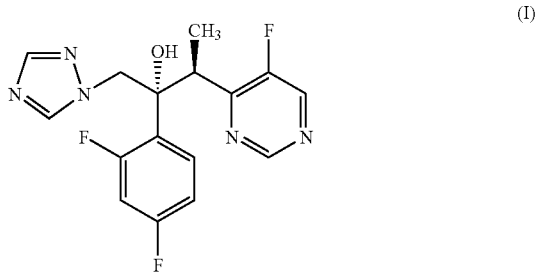

(I)

Voriconazole is a triazole antifungal agent. Voriconazole works principally by inhibition of cytochrome P450 14a-demethylase (P45014DM). This enzyme is in the sterol biosynthesis pathway that leads from lanosterol to ergosterol. Compared to fluconazole, voriconazole inhibits P45014DM to a greater extent. This inhibition is dose-dependent. Voriconazole is active following both oral and intravenous administrations. Oral (200 mg twice daily) and intravenous (3 to 6 mg/kg every 12 h) doses of Voriconazole have produced favorable response. Voriconazole is marketed under the name VFEND®. The VFEND® products are available as an I.V. solution, a powder for oral suspension (and hence an oral suspension), and film coated tablets for oral administration. VFEND® is for the treatment of some fungal infections. VFEND® is said to help fight life-threatening fungal infections, such as fungal infections in people who have a weak immune system, e.g., patients with cancer or patients who have received an organ or bone marrow transplant. VFEND® is said to have been proven effective against a type of fungus called Aspergillus. The following U.S. patents are listed in the U.S. FDA's Orange Book as to VFEND®: U.S. Pat. No. 5,116,844; U.S. Pat. No. 5,134,127; U.S. Pat. No. 5,364,938; U.S. Pat. No. 5,376,645; U.S. Pat. No. 5,567,817; U.S. Pat. No. 5,773,443; and U.S. Pat. No. 6,632,803. Formulations, doses and uses of Voriconazole as available commercially in the VFEND® product, and as in these herein cited US patents may be employed in the practice of the herein invention.

The '817 patent refers to different routes of synthesis for the preparation of Voriconazole and other triazole derivatives. One of these synthetic processes, as shown in schemes 1 and 2, comprises reacting 4-chloro-6-ethyl-5-fluoropyrimidine (compound II), which is deprotonated using a suitable base, such as LDA, with 1-(2,4-difluorophenyl)-2-(1H-1,2,4-triazol-1-yl)ethanone (compound III) in tetrahydrofuran. The product obtained in the above reaction is the following chloroderivative 3-(4-chloro-5-fluoropyrimidin-6-yl)-2-(2,4-difluorophenyl)-1-(1H-1,2,4-triazol-1-yl)butan-2-ol (compound IV) as a mixture of 4 stereoisomers, that is, 2 enantiomeric pairs, enantiomeric pair A (2R,3R/2S,3S) and enantiomeric pair B (2R,3S/2S,3R).

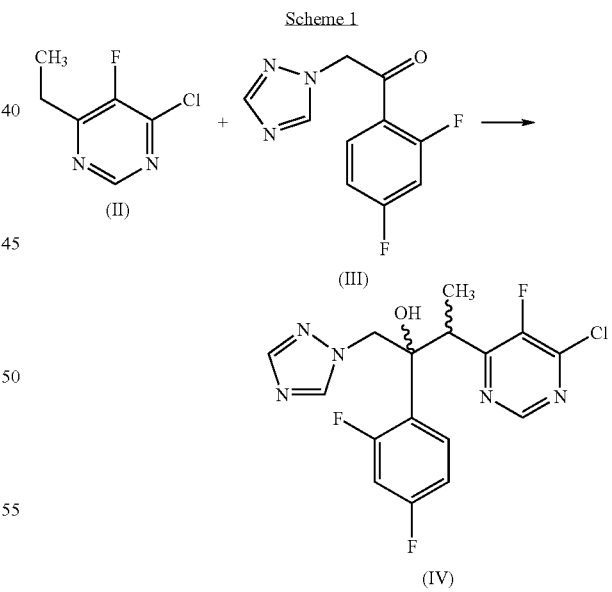

Scheme 1

The chromatographic treatment of the two pairs of enantiomers, A and B, allows the separation of enantiomeric pair B from enantiomeric pair A. Enantiomeric pair B of chloroderivative of formula (IV) is used then for obtaining Voriconazole (compound I).

Preparation of Racemic Voriconazole (Compound V) from Enantiomeric Pair B of chloroderivative of formula (IV) by classical hydrogenation conditions using Pd/C and sodium acetate in ethanol is shown in scheme 2. Resolution of the obtained racemic Voriconazole (compound V) is performed with (1R)-(−)-10-camphorsulfonic acid (CSA) in 38 volumes of methanol to give (2R,3S)-2-(2,4-difluorophenyl)-3-(5-fluoropyrimidin-4-yl)-1-(1H-1,2,4-triazol-1-yl)-butan-2-ol (1R)-(−)-10-camphorsulfonate (compound VI), that is, Voriconazole (1R)-(−)-10-camphorsulfonate, as hemimethanolate having a melting point of 176° C. Voriconazole (compound I) is isolated from Voriconazole (1R)-(−)-10-camphorsulfonate (compound VI) using dichloromethane and saturated aqueous sodium bicarbonate and final evaporation of the organic extract. The obtained Voriconazole shows a melting point of 127° C.

Scheme 2

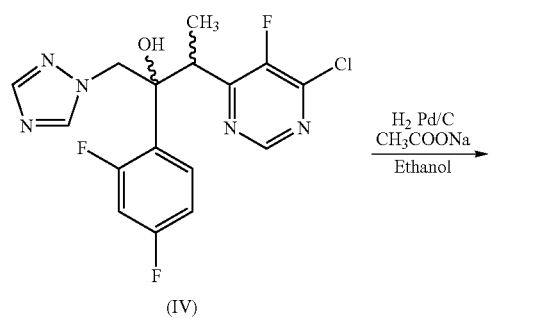

(IV)
Enantiomeric pair B

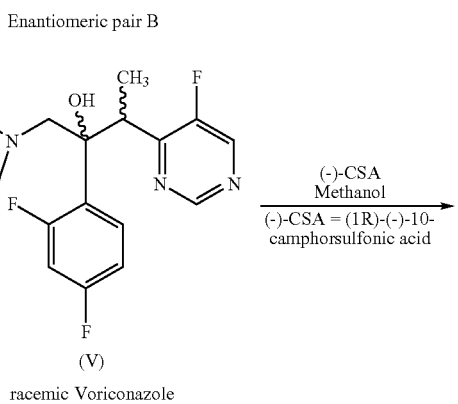

(V)
racemic Voriconazole

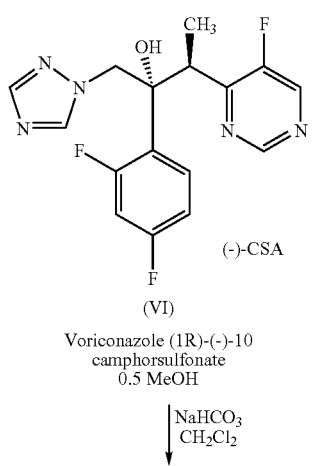

(VI)
Voriconazole (1R)-(−)-10 camphorsulfonate
0.5 MeOH

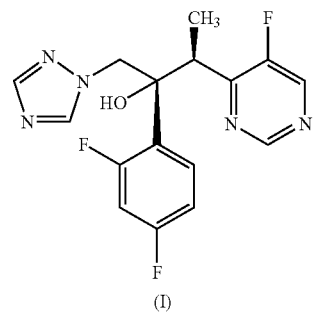

(I)
Voriconazole

Another process for the preparation of Voriconazole (compound I) is shown in scheme 3 in U.S. Pat. No. 6,586,594 (the '594 patent). The starting materials for the preparation of chloroderivative of formula (IV) are the same as in the '817 patent, but the pyrimidine derivative (compound II) is brominated at the methylene position of the ethyl group and the resulting bromopyrimidine derivative (compound VII) is used for the preparation of chloroderivative of formula (IV) by reaction with 1-(2,4-difluorophenyl)-2-(1H-1,2,4-triazol-1-yl)ethanone (compound III), as shown in scheme 3. In this case, the reaction is performed in the presence of zinc, iodine and/or a Lewis acid and an aprotic organic solvent, optionally also in the presence of lead. Using this process chloroderivative of formula (IV) as enantiomeric pair B is obtained with high stereoselectivity. Then, Voriconazole (compound I) is prepared from chloroderivative of formula (IV). The chloroderivative of formula (IV) can be used for the next step as free base or as acid addition salt, in particular, hydrochloride salt. In the '594 patent classical hydrogenation conditions using Pd/C and sodium acetate in ethanol is described. In '594 patent, catalytic transfer hydrogenation with HCOONH$_4$ is also described and exemplified starting from chloroderivative of formula (IV) as hydrochloride salt. In this case, two options are possible: direct dechlorination by using 4 equivalents of HCOONH$_4$ or previous alkaline treatment of the hydrochloride with NaOH in dichloromethane as extraction solvent and exchange of solvent with methanol. Resolution of racemic Voriconazole (compound V) is carried out with (1R)-(−)-10-camphorsulfonic acid ((−)-CSA) in a mixture (30 volumes) of acetone (22.5 volumes)/methanol (7.5 volumes) or in acetone (aprox. 10 volumes) followed by a treatment in a mixture of methanol and acetone. Voriconazole (compound I) is isolated from Voriconazole (1R)-(−)-10-camphorsulfonate (compound VI) using dichloromethane and 40% aqueous sodium hydroxide solution, evaporation of the organic extract and crystallization with isopropanol. The obtained Voriconazole has a melting point of 133° C.

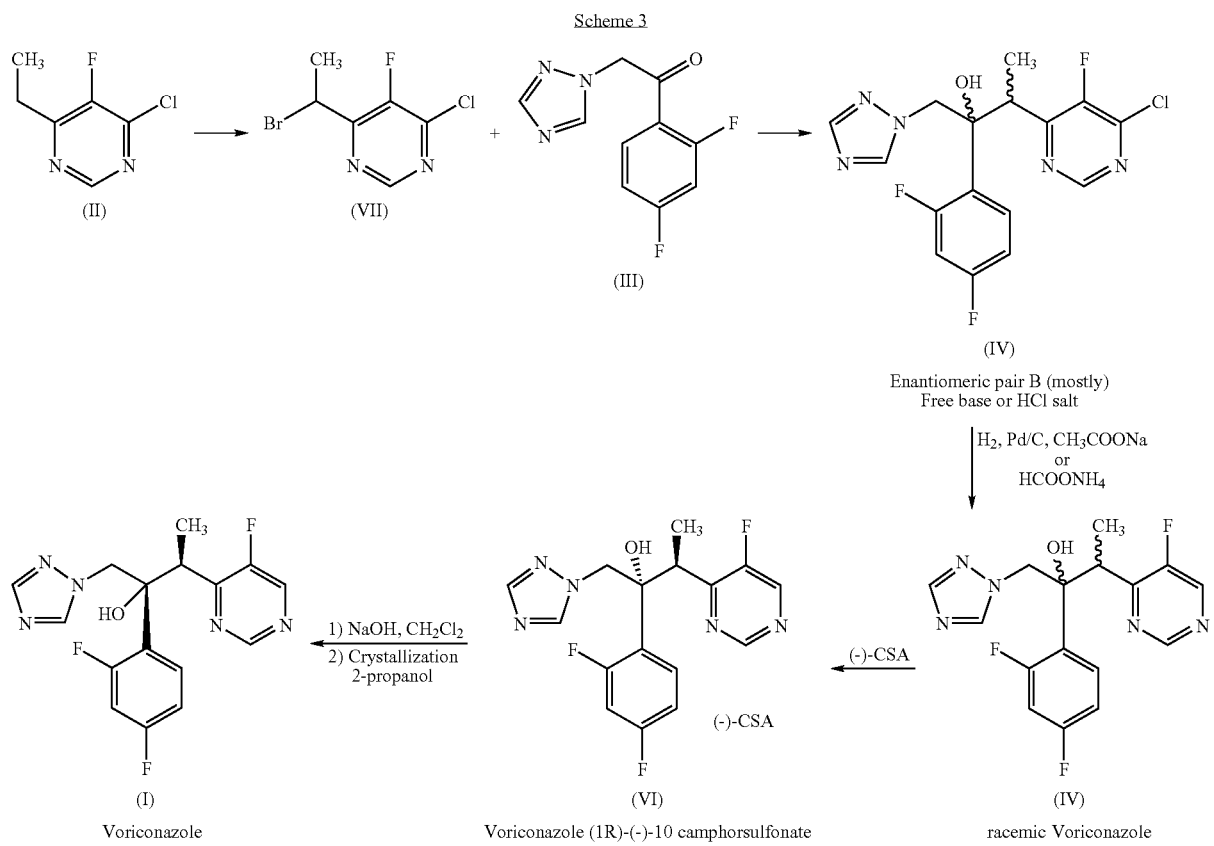

Scheme 3

(I) Voriconazole
(VI) Voriconazole (1R)-(−)-10 camphorsulfonate
(IV) racemic Voriconazole Polymorphism is very common among pharmaceutical substances. It is commonly defined as the ability of any substance to exist in two or more crystalline phases that have different arrangement and/or conformation of the molecules in the crystal lattice. Different polymorphs differ in their physical properties such as melting point, solubility, chemical reactivity, etc. These can appreciably influence pharmaceutical properties such as dissolution rate and bioavailability.

According to example 4ii of the '594 patent Voriconazole (compound I) is obtained with a melting point of 133° C. after a treatment with isopropanol followed by vacuum drying at 50° C. No polymorphic data are described in the '594 patent. However, this example has been reproduced by the herein inventors and the obtained product shows a X-ray powder diffractogram substantially identical to that of FIG. 1, an Infrared (IR) spectrum substantially identical to that of FIG. 2 and a Differential Scanning Calorimetry (open pan) substantially identical to that of FIG. 9. The obtained polymorphic form is designated herein as polymorphic Form I. FIG. 1 illustrates the X-ray powder diffractogram pattern (2θ) (±0.2°) of Voriconazole Form I comprising peaks at about 6.9°, 13.8°, 14.8°, 18.2°, 19.7°, 24.5°, 27.8° and 35.0°. X-ray powder diffractogram pattern of Voriconazole form I further comprises peaks at about 12.6°, 15.9°, 16.5°, 17.4°, 21.2°, 22.5°, 26.1°, 28.2° and 29.8°. FIG. 9 illustrates the differential scanning calorimetry (open pan) of Voriconazole form I which exhibits an endothermic peak at approximately 130° C.

The European Public Assessment Report for Vfend® of the European Medicine Agency (EMEA) mentions that "investigations into Voriconazole solid-state properties revealed no evidence of either polymorphism or solvates".

Crystalline polymorphic forms of Voriconazole (1R)-(−)-10-camphorsulfonate (compound VI) have not been reported in the literature. However, Voriconazole (1R)-(−)-10-camphorsulfonate crystal structure is described in the publication *Bioorganic & Medicinal Chemistry Letters*, 1996, 6, 2031. The corresponding crystal data and atomic positions can be retrieved from the Crystallographic Cambridge Data Base (refcode TUPFOZ). From these data a powder X-ray Diffraction pattern can be simulated, as shown in FIG. 7, assuming $CuK_\alpha$ radiation (for instance, using LAZY PULVERIX). This polymorphic form is designated herein as Form A. Voriconazole (1R)-(−)-10-camphorsulfonate Form A obtained by treating racemic Voriconazole (compound V) with (1R)-(−)-10-camphorsulfonic acid ((−)-CSA) in methanol shows a X-ray powder diffractogram substantially identical to that of FIG. 3 and an Infrared (IR) spectrum substantially identical to that of FIG. 4. FIG. 3 illustrates the X-ray powder diffractogram pattern (2θ) (0.2°) of Voriconazole (1R)-(−)-10-camphorsulfonate Form A comprising peaks at about 6.4°, 9.7°, 12.8°, 15.4°, 17.4°, 20.0°, 27.4° and 27.9°. X-ray powder diffractogram pattern of Voriconazole (1R)-(−)-10-camphorsulfonate Form A further comprises peaks at about 7.1°, 12.6°, 13.7°, 14.3°, 16.0°, 18.2°, 19.2°, 21.2°, 21.5°, 23.0°, 23.3°, 23.7°, 25.5° and 29.0°.

Some examples regarding particle size distribution of Voriconazole are found in the literature. U.S. Pat. No. 6,558,435 B2 describes a method of obtaining Voriconazole with an improved particle size from Voriconazole (1R)-(−)-10-camphorsulfonate by a technique consisting in mixing a solution of Voriconazole (1R)-(−)-10-camphorsulfonate in a mixture 50:50 volume ratio of ethanol/water with another solution of a base in such a way that both solutions are conducted separately through individual jets and contacted as jet streams in a vessel. The flow of the two solutions create an impingement zone between the two jets and crystalline material is formed and flowed down to another vessel. The particle size distribution achieved according to this methodology is 90% less than 41 μm and 50% less than 18 μm. It is also mentioned that the specification of product conventionally obtained by jet milling is 90% less than 130 μm and 50% less than 50 μm.

*IP.com Journal*, 2005, 5(6A), 38 (No. IPCOM000125373D) describes a method of preparing Voriconazole in a crystal habit which is particularly useful for making micronized Voriconazole by an air-jet mill or a pin-mill. Thus, Voriconazole is micronized to a particle size of about 40 μm, preferably about 20 μm.

In *Powder Technology*, 2004, 143-144, 179-185 nanoindentation of single particles is used as a technique to measure the mechanical properties of powders. Voriconazole with a particle size distribution of 90% less than 250 μm is analyzed. It is also mentioned that Voriconazole is very plastic and elastic.

In *Organic Process Research and Development*, 2004, 8, 674-679 nanoindentation of single crystals is used to predict milling of pharmaceutical materials including Voriconazole. It is mentioned that Voriconazole is very plastic and difficult to mill and that no size reduction below 250 μm could be obtained under standard mill types so a more energetic milling process is required.

SUMMARY OF THE INVENTION

Surprisingly, it has now been found that Voriconazole (1R)-(−)-10-camphorsulfonate can exist in a novel crystalline form, herein described as Form B.

The present invention provides for novel crystalline form B of Voriconazole (1R)-(−)-10-camphorsulfonate.

The present invention also provides for the preparation of this novel form of Voriconazole (1R)-(−)-10-camphorsulfonate.

Also, surprisingly, it has been found that Voriconazole can be obtained with small particle size distribution.

The present invention further provides for the use of Voriconazole of the invention as well as the Voriconazole from herein discussed processes for preparing Voriconazole, including in the preparation of a medicament for treating or preventing fungal infections, e.g., comprising admixing the Voriconazole with a carrier or diluent suitable for the treatment or prevention of fungal infections by Voriconazole, as well as in preparations or formulations for treating or preventing fungal infections comprising the Voriconazole and a carrier or diluent suitable for the use of Voriconazole for the treatment or prevention of fungal infections, and in methods for treating or preventing fungal infections comprising administering Voriconazole or a Voriconazole containing formulation or medicament.

The present invention provides an improved process of preparing Voriconazole and its intermediates.

The present invention also provides a method for obtaining a Voriconazole with a small particle size distribution.

More specifically, the invention relates to a process which comprises the dehalogenation of a haloderivative of Voriconazole via catalytic transfer hydrogenation of i.e (2R,3S/2S,3R)-3-(4-halo-5-fluoropyrimidin-6-yl)-2-(2,4-difluorophenyl)-1-(1H-1,2,4-triazol-1-yl)butan-2-ol to obtain racemic Voriconazole (i.e (2R,3S/2S,3R)-2-(2,4-difluorophenyl)-3-(5-fluoropyrimidin-4-yl)-1-(1H-1,2,4-triazol-1-yl)butan-2-ol). Thereafter, racemic Voriconazole (compound V) is resolved using (1R)-(−)-10-camphorsulfonic acid ((−)-CSA) and isolating Voriconazole (compound I) from the diastereomeric salt Voriconazole (1R)-(−)-10-camphorsulfonate (compound VI).

The present invention provides significant improvements over the processes described in the literature for preparing Voriconazole.

For instance, the improved process of the instant invention avoids the use of undesirable solvents such as dichloromethane or ether in the preparation of racemic Voriconazole (compound V) from haloderivative of Voriconazole.

The invention further advantageously avoids the use of undesirable solvents such as dichloromethane in the isolation step of Voriconazole (compound I) from Voriconazole (1R)-(−)-10-camphorsulfonate (compound VI).

The invention also eliminates the need for chromatographic treatments.

The whole process has been simplified by means of the no isolation of racemic Voriconazole (compound V).

Furthermore, in the resolution step the amount of solvent has been substantially reduced in comparison with previous processes.

The present invention further relates to a process for the preparation of Voriconazole, with high enantiomeric and chemical purity, e.g., enantiomeric and/or chemical purity >95%, such as enantiomeric and/or chemical purity of from about 96.50% to about 99.50%, e.g., enantiomeric and/or chemical purity >97.00%, for example enantiomeric purity >97.00% and chemical purity >99.50% such as enantiomeric purity between about 97.50% to about 100.00% and chemical purity between about 99.95% to about 100.00%.

The present invention also relates to a process for the preparation of Voriconazole (1R)-(−)-10-camphorsulfonate salt crystalline Form A with high enantiomeric and chemical purity, e.g., treating racemic Voriconazole with a chiral resolving acid in an alcohol or mixtures of an alcohol, e.g., a $C_1$-$C_6$ alcohol, such as methanol, ethanol, isopropanol or 1-butanol, and another organic solvent(s), e.g., $C_1$-$C_6$ acetate such as ethyl acetate.

The present invention comprises a new polymorphic form of Voriconazole (1R)-(−)-10-camphorsulfonate designated herein as Form B with high enantiomeric and chemical purity, e.g., enantiomeric purity >97.00% and chemical purity is >99.50% such as enantiomeric purity between about 97.50% to about 99.95% and chemical purity between about 99.95% to about 100.00%.

The present invention also relates to a process for the preparation of Voriconazole (1R)-(−)-10-camphorsulfonate salt crystalline Form B with high enantiomeric and chemical purity. The process comprises drying at 50-60° C. under vacuum wet Voriconazole (1R)-(−)-10-camphorsulfonate.

The present invention also provides an advantageous and straightforward method of obtaining Voriconazole with small particle size distribution compared to the methods described in the literature, without the need of any special equipment or technique.

The present invention also provides Voriconazole having a particle size distribution wherein 10% of the total volume is made of particles having a diameter of about 6 μm or below, 50% of the total volume is made of particles having a diameter of about 20 μm or below and 90% of the total volume is made of particles having a diameter of about 40 μm or below.

The process for obtaining Voriconazole with small particle size distribution can comprise treating Voriconazole (1R)-(−)-10-camphorsulfonate (compound VI) in an aqueous solvent with a suitable base at a temperature preferably between room temperature and below 55° C., cooling the suspension to approximately 20° C. to 25° C., filtering the obtained solid, washing it with water and drying the solid to obtain Voriconazole (compound I) with small particle size distribution.

Accordingly, it is an object of the invention to not encompass within the invention any previously known product, process of making the product or method of using the product such that applicant(s) reserve the right and hereby disclose a disclaimer of any previously known processes.

Terms "comprising" and "comprises" in this disclosure can mean "including" and "includes" or can have the meaning commonly given to the term "comprising" or "comprises" in US Patent Law. Terms "consisting essentially of" or "consists essentially of" if used in the claims have the meaning ascribed to them in US Patent Law. Other aspects of the invention are described in or are obvious from (and within the ambit of the invention) the following disclosure.

These and other embodiments are disclosed or are apparent from and encompassed by, the following Detailed Description.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION

Figure 1:
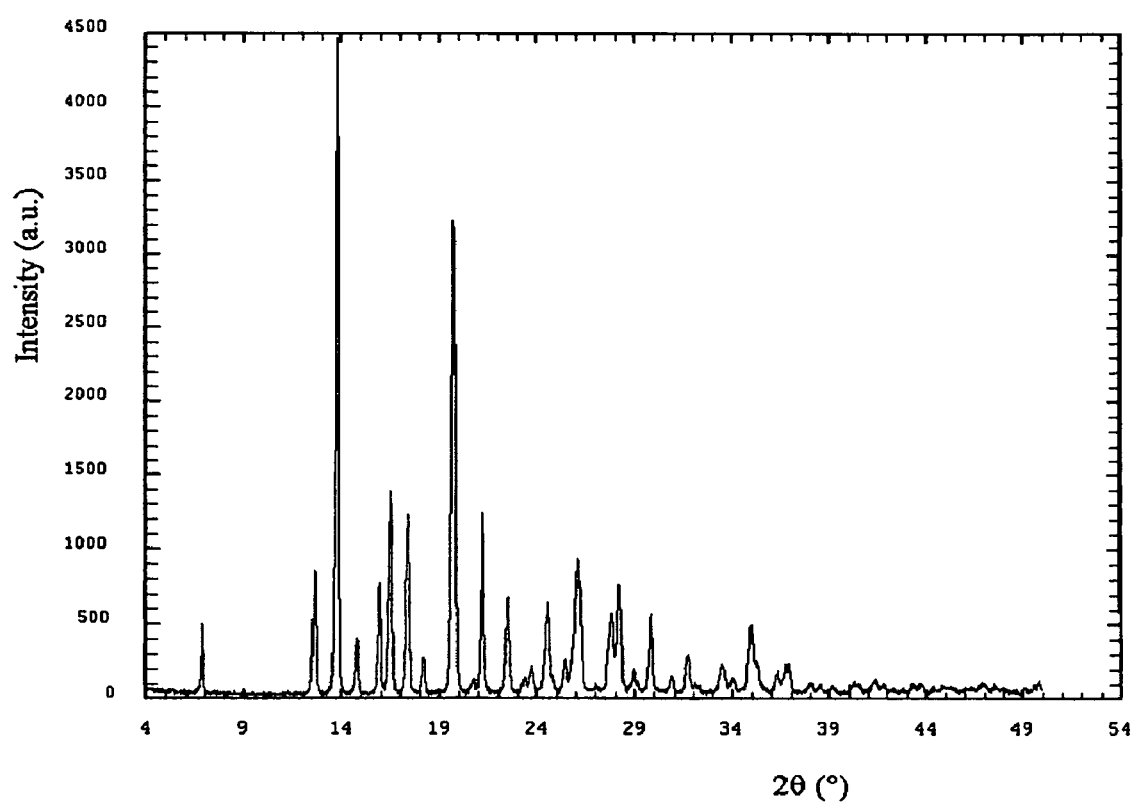
FIG. 1: illustrates the X-ray powder diffractogram (XRD) of Voriconazole Form I obtained in example 10.

Reference will now be made in detail to various embodiments of the invention. This invention may, however, be embodied in many different forms and should not be construed as limited to the embodiments set forth herein.

The present invention relates to an improved process for the preparation of Voriconazole (compound I):

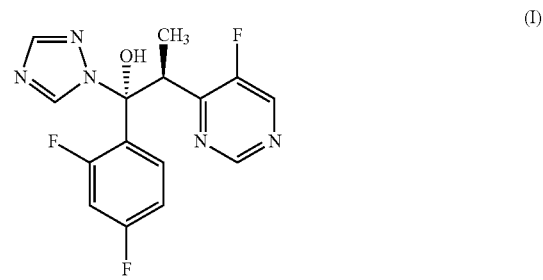

which comprises:
(a) dehalogenation under catalytic transfer hydrogenation of a compound of formula (IV):

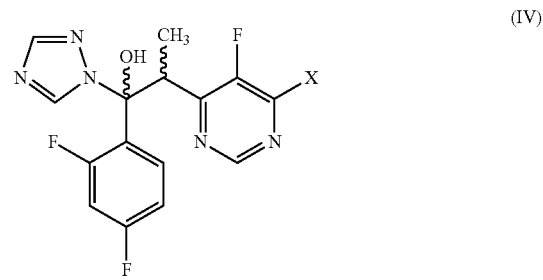

wherein, X is halogen and the compound of formula (IV) is a free base, salt thereof or mixture of free base and salt, to form a racemic mixture of Voriconazole (compound V):

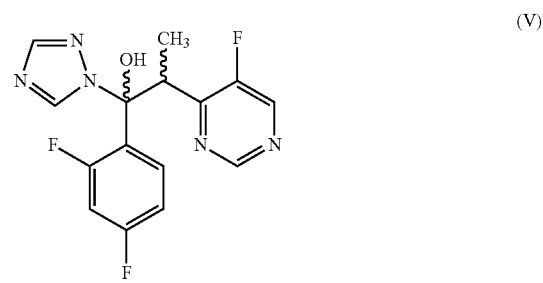

(b) resolving the racemic mixture of Voriconazole (compound (V)) by treatment of said racemic mixture with a chiral resolving acid in an alcohol or mixture of an alcohol with an additional organic solvent to form compound (VI) which is a diastereomeric salt of the chiral resolving agent with Voriconazole; and
(c) optionally drying compound (VI); and
(d1) treating the compound (VI) with a non-chlorinated organic solvent and an aqueous alkaline solution to form Voriconazole; or
(d2) treating the compound (VI) in aqueous solution with a base to form Voriconazole, with small particle size distribution.

In one embodiment of the invention, the process for the preparation of Voriconazole, by treating Voriconazole (1R)-

(−)-10-camphorsulfonate with a non-chlorinated organic solvent and an aqueous alkaline solution, wherein the Voriconazole (1R)-(−)-10-camphorsulfonate is obtained by a process comprises:
(a) dehalogenation of

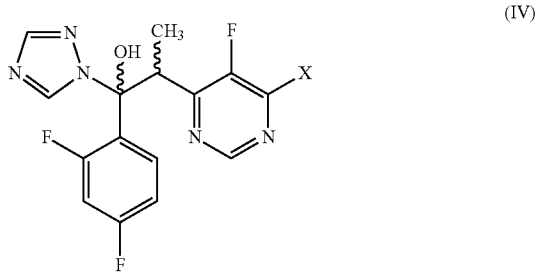

(IV)

under catalytic transfer hydrogenation by using a catalyst in a solvent, wherein the obtained racemic Voriconazole is not isolated,
(b) reacting the racemic Voriconazole with (1R)-(−)-10-camphorsulfonic acid in methanol,
(c) optionally drying the obtained Voriconazole (1R)-(−)-10-camphorsulfonate.

In another embodiment of this process, the dehalogenation is a dechlorination; X is chlorine and catalytic transfer hydrogenation is accomplished by using ammonium formate and Pd/C catalyst in a solvent selected from the group consisting of esters and alcohols, preferably $C_1$-$C_6$ esters and $C_1$-$C_6$ alcohols, more preferable ethyl acetate and methanol. In still another embodiment of the invention, the solvent is ethyl acetate.

The invention includes a process for preparation of Voriconazole (compound I) generally comprising the dehalogenation under catalytic transfer hydrogenation of a compound of formula (IV):

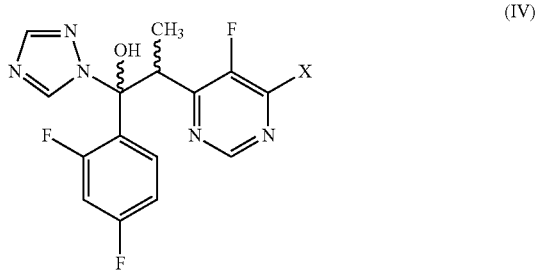

(IV)

wherein X is halogen and the compound of formula (IV) is a free base, salt thereof or mixture of free base and salt. In one embodiment of this invention, the dehalogenation is a dechlorination; X is chlorine and catalytic transfer hydrogenation is accomplished by using ammonium formate and Pd/C catalyst in a suitable solvent.

When the salt of compound IV is used, a previous alkaline treatment is carried out to obtain compound IV as free base in solution. In one embodiment of this invention, the salt is a hydrochloride salt of compound IV and is treated with ethyl acetate (3 volumes of ethyl acetate with respect to compound IV as free base) and an aqueous solution of sodium bicarbonate, thereafter the organic phase containing compound IV as free base is separated and directly used in the dehalogenation reaction with ammonium formate and Pd/C catalyst.

In one embodiment of this invention, the suitable organic solvent in the dehalogenation reaction is selected from esters or alcohols. In another embodiment of this invention, when the reaction is a dechlorination reaction, the solvent is an ester solvent, preferably ethyl acetate. In yet another embodiment of this invention the suitable solvent is an alcoholic solvent which includes but is not limited to $C_1$-$C_6$ alcohol such as methanol, ethanol, isopropanol and 1-butanol with a preferred embodiment being methanol.

The dehalogenation reaction is conducted between about 60° C. and reflux temperature, preferably between about 60° C. and about 70° C. until completion of the reaction, the mixture is cooled to about 20° to about 40°, the catalyst is filtered and the filtrate is treated to give racemic Voriconazole (compound V):

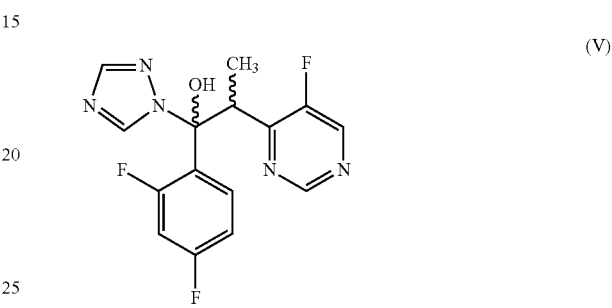

(V)

The racemic Voriconazole filtrate may be treated according to several options. One option can include washing the filtrate with a neutral or alkaline aqueous medium and concentrating to dryness. Preferably, this crude residue is used for the resolution step without is further purification but optionally can be purified. Another option can include concentrating to dryness and purifying the obtained crude by crystallisation. Preferably, part of the solvent of the filtrate is distilled and after cooling to about 20° C. to about 25° C. a suspension of racemic Voriconazole (compound V) is obtained.

The invention further includes the resolution of racemic Voriconazole (compound V) obtained through the process described above which comprises the treatment of racemic Voriconazole with a chiral resolving acid in an alcohol or mixtures of an alcohol, e.g., a $C_1$-$C_6$ alcohol, such as methanol, ethanol, isopropanol or 1-butanol and another organic solvent(s), e.g., $C_1$-$C_6$ acetate such as ethyl acetate. In one embodiment of the invention, the alcohol is methanol.

The resolution mixture is heated until solution, allowed to cool to a suitable temperature, stirred at that temperature for a suitable time and the suspension formed is filtrated, to give the corresponding diastereomeric salt of the chiral resolving acid. When the chiral resolving acid is (1R)-(−)-10-camphorsulfonic acid and the solvent is advantageously methanol, the obtained diastereomeric salt corresponds to Voriconazole (1R)-(−)-10-camphorsulfonate (compound VI)−(−)-CSA= (1R)-(−)-10-camphorsulfonic acid.

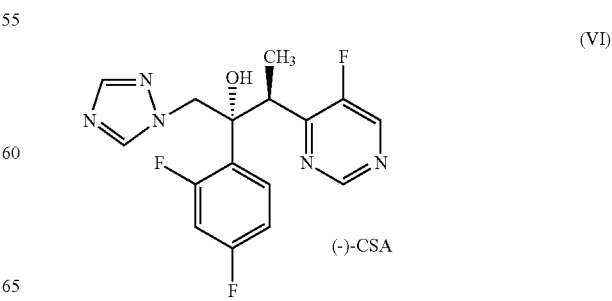

(VI)

In one embodiment of this invention, the resolution step is carried out by treating a suspension of racemic Voriconazole (compound V) in ethyl acetate with (1R)-(−)-10-camphorsulfonic acid in methanol, followed by an azeotropic distillation of the remaining ethyl acetate together with methanol and allowing the mixture in the resolution conditions to obtain a suspension of Voriconazole (1R)-(−)-10-camphorsulfonate (compound VI) in methanol. Preferably, the resolution conditions involve a final amount of methanol of 10 volumes with respect to racemic Voriconazole (compound V). The suspension is stirred between about 20° C. and about 25° C. and filtered to obtain Voriconazole (1R)-(−)-10-camphorsulfonate (compound VI).

The obtained Voriconazole (1R)-(−)-10-camphorsulfonate (compound VI) corresponds to Voriconazole (1R)-(−)-10-camphorsulfonate Form A with high enantiomeric and chemical purity. In one embodiment of this invention the enantiomeric purity and chemical purity of Form A is >95%. In another embodiment of this invention, the enantiomeric purity is about 96.50% to about 99.50%. When Voriconazole (1R)-(−)-10-camphorsulfonate is dried between about 50 to about 60° C. under vacuum, Voriconazole (1R)-(−)-10-camphorsulfonate Form B is obtained.

Optionally, additional purification steps can be included without altering the invention. In particular additional steps can include treating the obtained Voriconazole (1R)-(−)-10-camphorsulfonate with methanol, heating the mixture, cooling the solution to approximately 0-5° C. and isolating the resulting solid by filtration. The process can be repeated as necessary.

Another aspect of the invention further includes the use of Voriconazole (1R)-(−)-10-camphorsulfonate (compound VI), obtained as previously described, for the isolation of Voriconazole (compound I).

The isolation of Voriconazole comprises the treatment of Voriconazole (1R)-(−)-10-camphorsulfonate (compound VI) with a non-chlorinated organic solvent and an aqueous alkaline solution. The non-chlorinated organic solvents include but are not limited to the esters with a preferred embodiment being ethyl acetate.

The inorganic base is selected from hydroxides of alkali metals or hydroxides of alkaline earth metals, carbonates or bicarbonates of alkali metals or carbonates or bicarbonates of alkaline earth metals. A preferred inorganic base is sodium bicarbonate. Preferably, Voriconazole (1R)-(−)-10-camphorsulfonate (compound VI) is treated with ethyl acetate and an aqueous sodium bicarbonate solution. The organic phase is separated and optionally washed one or more times with water. Additional steps can include treating the organic solution with a decolorizing agent to improve the color and appearance of the resulting crystals and/or additional filtration steps to remove impurities (e.g., insolubles).

The decolorizing agent can be any conventional decolorizing agent, including, for example, alumina, activated alumina, silica and charcoal. Both the addition of the decolorizing agent and/or any additional filtration steps can be conducted at a temperature preferably between room temperature and below the reflux temperature of the organic solvent, preferably below 77° C. The organic solution containing Voriconazole (compound I) is partially distilled, the obtained residue is treated with an alcoholic solvent and partially distilled to obtain Voriconazole as a residue. The preferred alcoholic solvent is isopropanol. Thereafter the residue is crystallized from an alcoholic solvent, filtered and dried. The preferred alcoholic solvent is isopropanol.

Alternatively, the isolation of Voriconazole comprises the treatment of Voriconazole (1R)-(−)-10-camphorsulfonate (compound VI) in an aqueous solvent with a suitable base at a temperature preferably between room temperature and below 55° C., cooling the suspension to approximately 20° C. to 25° C., filtering the obtained solid, washing it with water and drying the solid to obtain Voriconazole (compound I). Voriconazole obtained following this process has a small particle size distribution.

Aqueous solvents include but are not limited to water. Suitable bases are organic bases and inorganic bases. In one embodiment of this invention, the organic base is a dialkylamine or trialkylamine. In another embodiment of the invention, the inorganic base is a carbonate or bicarbonate of an alkali metal or a carbonate or bicarbonate of an alkaline earth metal. A further embodiment of the invention, the inorganic base is a hydroxide of alkali metal or hydroxide of alkaline earth metal. A preferred organic base is triethylamine. Preferred inorganic base is sodium carbonate.

The obtained Voriconazole is characterized by having small particle size distribution. In one embodiment of the invention the Voriconazole obtained has a particle size distribution wherein about 5-15% of the total volume is made of particles having a diameter of about 6 μm or below, about 45-55% of the total volume is made of particles having a diameter of about 20 μm or below and about 85-95% of the total volume is made of particles having a diameter of about 40 μm or below.

In another embodiment of the invention the Voriconazole obtained has a particle size distribution wherein about 8-12% of the total volume is made of particles having a diameter of about 6 μm or below, about 48-52% of the total volume is made of particles having a diameter of about 20 μm or below and about 88-92% of the total volume is made of particles having a diameter of about 40 μm or below.

In still another embodiment of this invention, Voriconazole is obtained having a particle size distribution wherein 10% of the total volume is made of particles having a diameter of about 6 μm or below, 50% of the total volume is made of particles having a diameter of about 20 μm or below and 90% of the total volume is made of particles having a diameter of about 40 μm or below.

The obtained Voriconazole is characterized by having a high enantiomeric purity and a high chemical purity. In one embodiment of this invention, the enantiomeric purity is >97.00% and the chemical purity is >99.50%. In another embodiment of this invention, the enantiomeric purity is between about 97.50% to about 100.00% and chemical purity is between about 99.95% to about 100.00%.

The invention further comprises a new polymorphic crystalline form of Voriconazole (1R)-(−)-10-camphorsulfonate designated herein as Voriconazole (1R)-(−)-10-camphorsulfonate form B and methods of making it.

Figure 5:
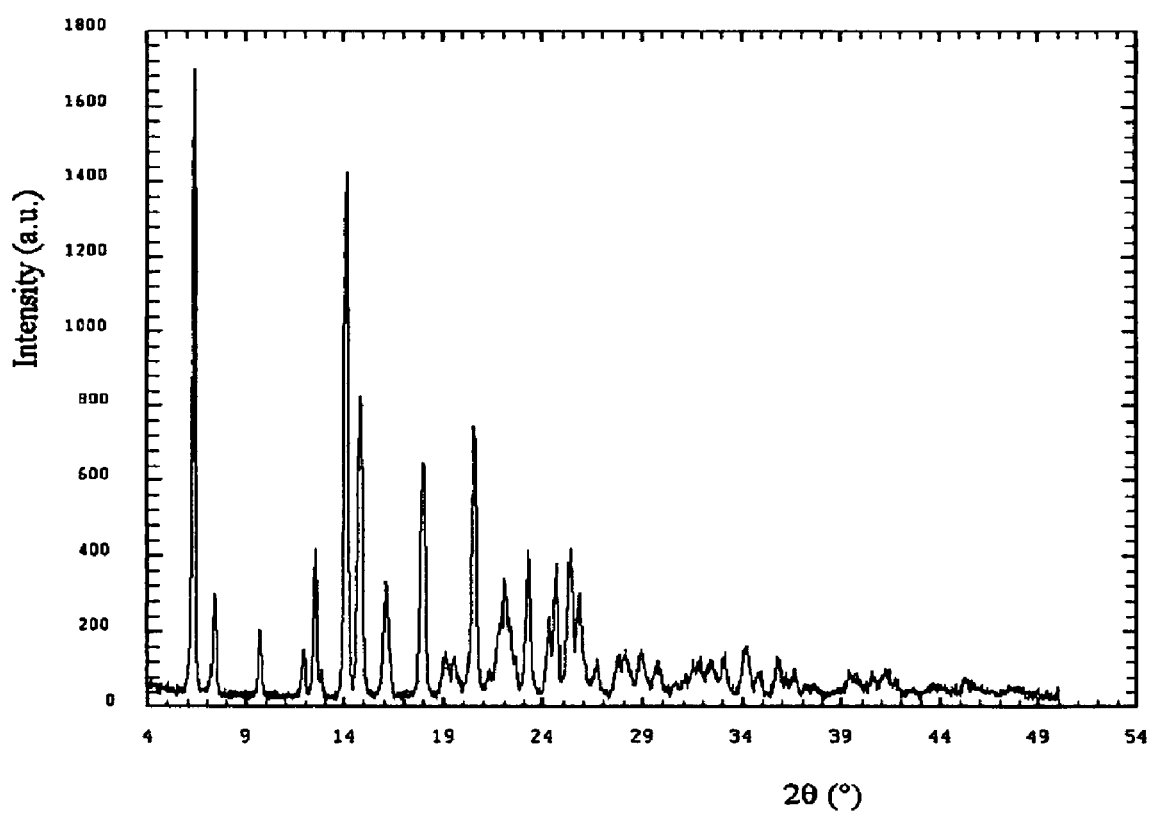
FIG. 5: illustrates the X-ray powder diffractogram (XRD) of Voriconazole (1R)-(−)-10-camphorsulfonate Form B obtained in example 1.

Voriconazole (1R)-(−)-10-camphorsulfonate form B is characterized by having an X-ray powder diffractogram pattern substantially identical to that of FIG. 5. FIG. 5 illustrates the X-ray powder diffractogram pattern (2θ) (±0.2°) of Voriconazole (1R)-(−)-10-camphorsulfonate Form B comprising peaks at about 6.4°, 7.4°, 14.1°, 14.7°, 14.9°, 20.6°, 24.3° and 24.6°. X-ray powder diffractogram pattern of Voriconazole (1R)-(−)-10-camphorsulfonate Form B further comprises peaks at about 9.7°, 12.5°, 16.1°, 18.0°, 22.1°, 23.2°, 25.4° and 25.8°.

Figure 6:
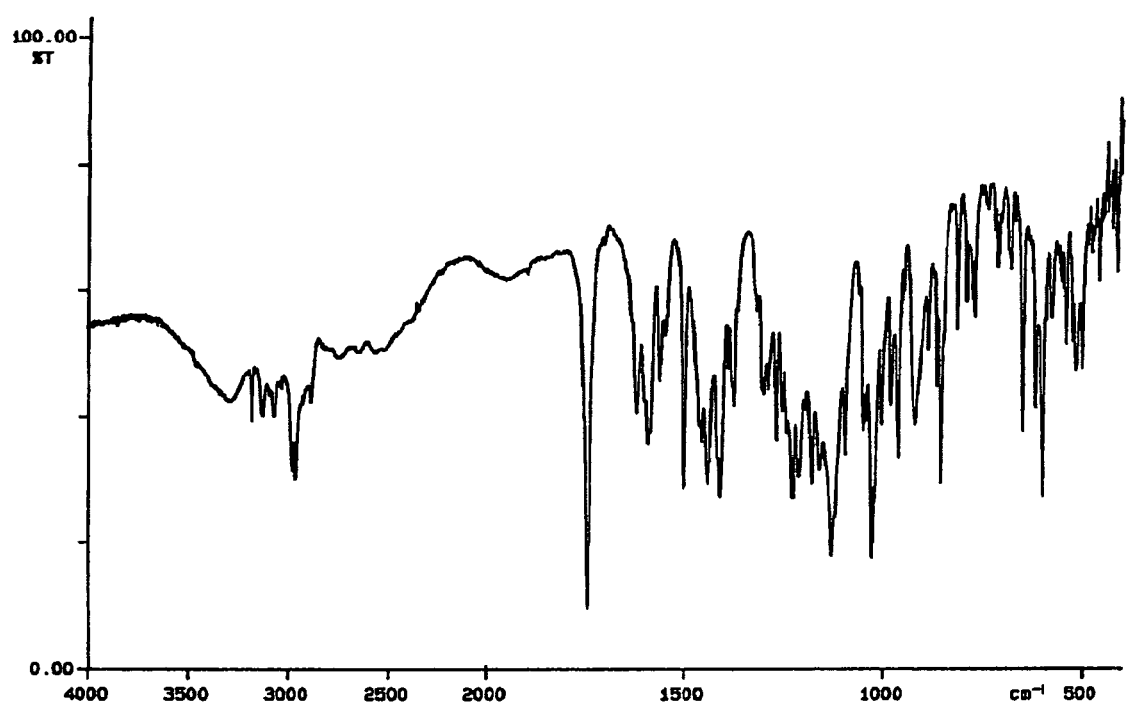
FIG. 6: illustrates the Infrared (IR) spectrum of Voriconazole (1R)-(−)-10-camphorsulfonate Form B obtained in example 1
Figure 7:
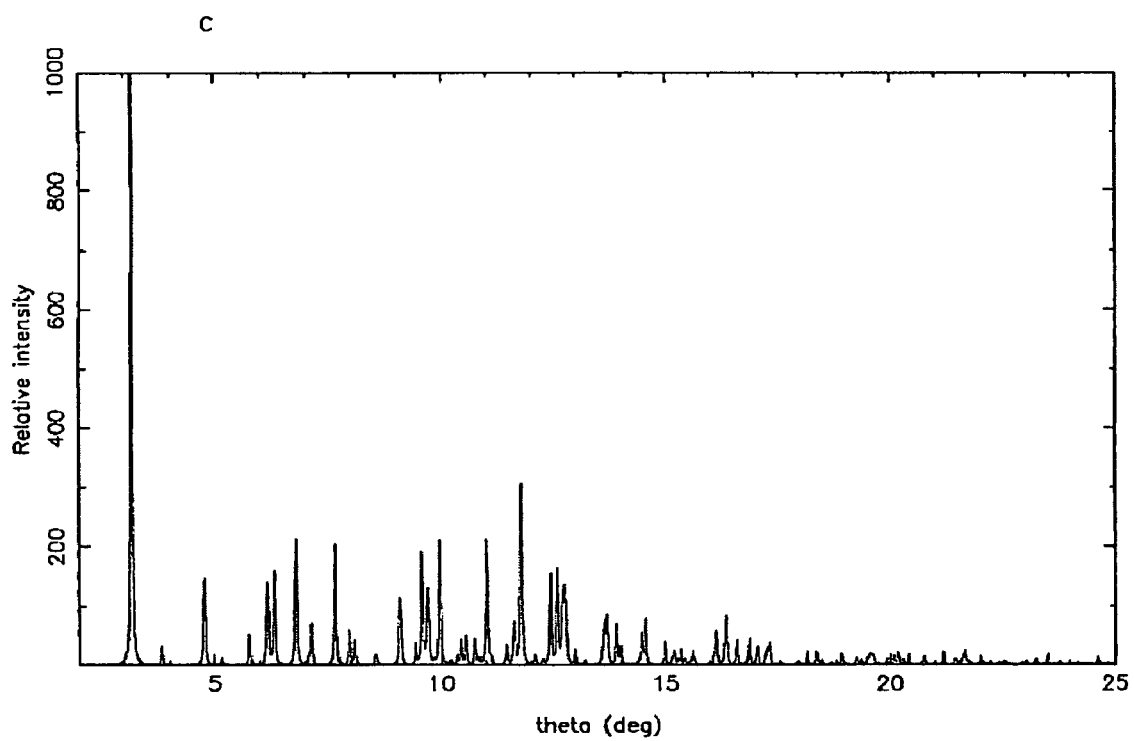
FIG. 7: illustrates the simulated X-ray powder diffractogram (XRD) of Voriconazole (1R)-(−)-10-camphorsulfonate Form A.
Figure 8:
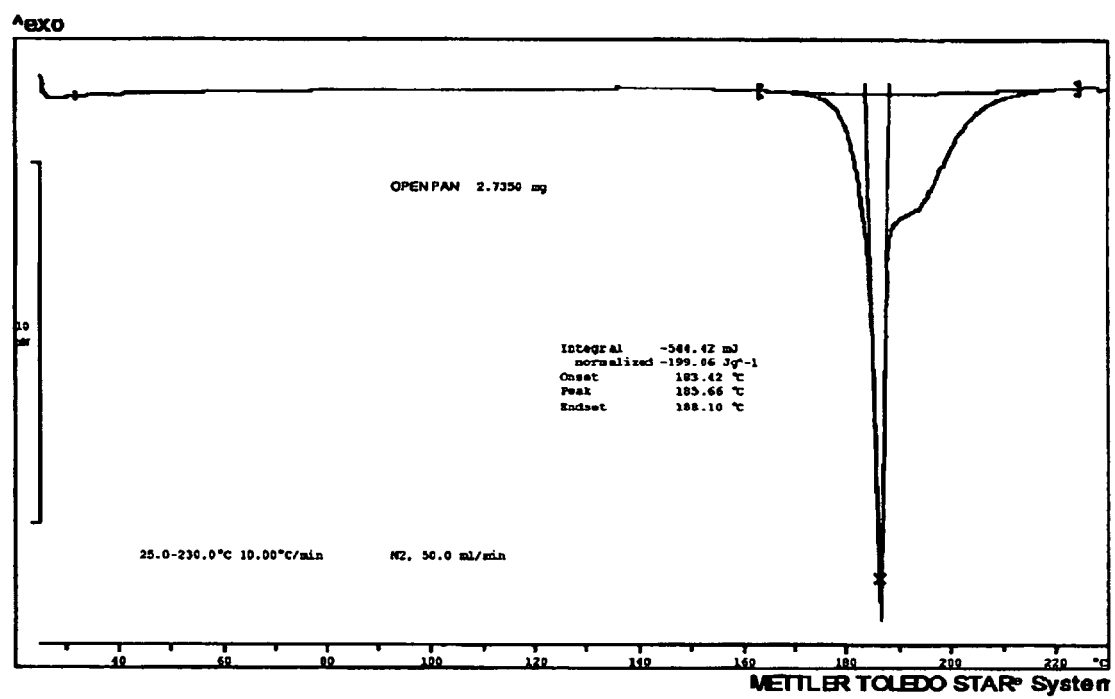
FIG. 8: illustrates the Differential Scanning Calorimetry (DSC) thermogram in an open pan of Voriconazole (1R)-(−)-10-camphorsulfonate of Form B obtained in example 1.

FIG. 6 illustrates the Infrared (IR) spectrum of Voriconazole (1R)-(−)-10-camphorsulfonate Form B. FIG. 8 illustrates the differential scanning calorimetry (open pan) of Voriconazole (1R)-(−)-10-camphorsulfonate Form B which exhibits an endothermic peak at approximately 185° C.

The invention further includes a process for preparing Voriconazole (1R)-(−)-10-camphorsulfonate form B generally comprising drying at 50-60° C. under vacuum wet Voriconazole (1R)-(−)-10-camphorsulfonate. The Voriconazole (1R)-(−)-10-camphorsulfonate form B formed also has high enantiomeric purity and high chemical purity. In one embodiment of this invention, the enantiomeric purity is >97% and the chemical purity is >99.00%. In another embodiment of this invention, the enantiomeric purity is between about 97.00% and about 99.00% and the chemical purity is between about 99.00% and 100.00%.

The invention further includes Voriconazole with small particle size distribution wherein 10% of the total volume is made of particles having a diameter of about 6 μm or below, 50% of the total volume is made of particles having a diameter of about 20 μm or below and 90% of the total volume is made of particles having a diameter of about 40 μm or below.

The invention is further described by the following non-limiting examples which further illustrate the invention, and are not intended, nor should they be interpreted to, limit the scope of the invention.

EXAMPLES

General Experimental Conditions i. X-Ray Powder Diffraction (XRD)

The X-ray diffractograms were obtained using a RX SIEMENS D5000 diffractometer with a vertical goniometer and a copper anodic tube, radiation $CuK_\alpha$, λ=1, 54056 Å.

ii. Infrared Spectra

Fourier transform infrared spectra were acquired on a Perkin-Elmer 1600 series FTIR spectrometer and polymorphs were characterized in potassium bromide pellets.

iii. Differential Scanning Calorimetry (DSC)

DSC measurements were carried out in vented pan at a scan rate of 10° C./minute from 25.0° C. to 230.0° C. or 140° C. under a nitrogen purge with a METTLER-TOLEDO DSC 821.

iv. HPLC Method

HPLC, Method A:

The chromatographic separation is carried out in a Daicel CHIRALCEL OD-H, 5 μm, 4.6 mm×250 mm column.

The mobile phase is prepared by mixing 850 ml of hexane with 150 ml of ethanol.

The chromatograph is equipped with a 254 nm detector and the flow rate is 1.0 ml/min at 20-25° C. Inject 10 μl of the tests samples prepared dissolving 25 mg of sample in 25 ml of mobile phase.

HPLC, Method B:

The chromatographic separation is carried out in a Symmetry C18, 3.5 μm, 4.6 mm×100 mm column.

The mobile phase A is a 0.010 M ammonium formate buffer, pH 4.0, which is prepared from 0.63 g of $HCOONH_4$ dissolved in 1000 ml of water, adjusting pH to 4.0 with formic acid. The mobile phase is mixed and filtered through a 0.22 μm nylon membrane under vacuum.

The mobile phase B is acetonitrile.

The chromatograph is programmed as follows:

Initial 0-8 min. 70% mobile phase A, 8-20 min. linear gradient to 20% mobile phase A, 2040 min. isocratic 20% mobile phase A, 40-45 min. linear gradient to 70% mobile phase A and 45-55 min. equilibration with 70% mobile phase A.

The chromatograph is equipped with a 254 nm detector and the flow rate is 1.0 ml per minute at 20-25° C. Inject 20 μl of the test samples prepared dissolving 50 mg of sample in 25 ml of acetonitrile.

HPLC, Method C:

The chromatographic separation is carried out in a Kromasil 100Si, 5 μm, 4.6 mm×250 mm column.

The mobile phase is prepared by mixing 850 ml of hexane with 150 ml of ethanol.

The chromatograph is equipped with a 254 nm detector and the flow rate is 1.0 ml/min at 20-25° C. Inject 20 μl of the tests samples prepared dissolving 25 mg of sample in 25 ml of mobile phase.

HPLC, Method D:

The chromatographic separation is carried out in a Symmetry C18, 3.5 μm, 4.6 mm×150 mm column.

The mobile phase A is a 0.010 M ammonium formate buffer, pH 4.0, which is prepared from 0.63 g of $HCOONH_4$ dissolved in 1000 ml of water, adjusting pH to 4.0 with formic acid. The mobile phase is mixed and filtered through a 0.22 μm nylon membrane under vacuum.

The mobile phase B is acetonitrile.

The chromatograph is programmed as follows:

Initial 0-13 min. 75% mobile phase A, 13-25 min. linear gradient to 40% mobile phase A, 25-35 min. isocratic 40% mobile phase A, 35-40 min. linear gradient to 25% mobile phase A, 40-55 min. isocratic 25% mobile phase A, 55-60 min. linear gradient to 75% mobile phase A and 60-65 min. equilibration with 75% mobile phase A.

v. Gas Chromatography

Chromatographic separation was carried out in a TRB-624 capillary column of 1.8 Win film thickness, 75 m×0.53 mm i.d. column. The chromatograph was equipped with a FID detector and a Head Space injection auxiliary device.

The oven temperature is programmed as follows: Initial 0-20 min. 40° C., then the temperature was raised to 225° C. (ramp rate 5°/minute) and was maintained at 225° C. for 5 minutes. The injector and detector temperatures were set at 225° C. and 250° C. respectively. Helium was used as carrier gas at a pressure of 7 psi with a split. Samples were heated for 45 minutes at 80° C. in the head space device. After heating, the vials were pressurized with helium at 18 psi for 0.2 minutes. The sample loop was filled for 0.2 minutes (loop volume=3 mL.) and then injected for 1 minute.

Solutions:

Standard solvents Solution (100 ppm): Dilute quantitatively 100 mg of solvent with 100 mL of dimethyl sulfoxide and dilute 1 mL of this solution to 10 mL with dimethyl sulfoxide to obtain a solution containing 0.01 μg./mL.

Test solution: Prepare a solution of about 200 mg. of Voriconazole test sample in 5 mL of dimethyl sulfoxide.

Procedure: The vials were sealed with suitable crimp caps and analyzed by head space using the above-described conditions. A blank run was performed using dimethylsulfoxide and then disregarding the peaks corresponding thereto in the test and standard solution runs.

vi. Assay

Weigh accurately about 350 mg of sample; dissolve in 70 ml of glacial acetic acid. Titrate with 0.1 N $HClO_4$ VS determining the end point potentiometrically fitting the increases of volume to 0.05 ml in the proximities of equivalence point. Each ml of 0.1 N $HClO_4$ VS is equivalent to 34.93 mg of Voriconazole.

vii. Particle Size Distribution

Particle size measurement was obtained using a Malvern particle size analyser equipped with a 2 milliwatt Helium/Neon laser and a Fourier Transform lens system. The sample was run using the 2.40 mm lens. The sample unit was a MS1-Small Volume Sample Dispersion Unit stirred cell. The dispersant was DI water. The sample particle size distribution was assumed to follow a normal distribution.

Analysis model: polydisperse.
Setup presentation: standard wet (30HD)
Particle R.I.=(1.5295, 0.1)
Dispersant R.I.=1.33
Procedure:

1 ml of Tween 20 was diluted to 1000 ml with water (solution 0.1% of Tween 20 in DI water). Approximately 250 mg of sample was dispersed in 20 ml of the solution 0.1% of Tween 20 in DI water. This sample was sonicated for 2 minutes and delivered dropwise to the previously filled and background corrected measuring cell until the desired obscuration was reached.

This dispersion (the dispersion in the stirring measuring cell) was measured after stabilization of the obscuration.

Example 1

Preparation of Voriconazole
(1R)-(−)-10-camphorsulfonate Form B

To a suspension of (2R,3S/2S,3R)-3-(4-chloro-5-fluoropyrimidin-6-yl)-2-(2,4-difluorophenyl)-1-(1H-1,2,4-triazol-1-yl)butan-2-ol hydrochloride (100 g, 94.2% HPLC purity, 0.224 mol) in ethyl acetate (270 ml) was added slowly aqueous saturated sodium bicarbonate solution (200 ml). The mixture was stirred for 15 minutes, the phases allowed to settle and the aqueous layer separated. The organic layer, which contained (2R,3S/2S,3R)-3-(4-chloro-5-fluoropyrimidin-6-yl)-2-(2,4-difluorophenyl)-1-(1H-1,2,4-triazol-1-yl)butan-2-ol as free base, was added to a mixture of ammonium formate (28.3 g, 0.448 mol) and wet (54.9% moisture) 10% Pd/C catalyst (3.81 g), heated to 60-65° C. and stirred at this temperature for 2 hours and 30 minutes. The mixture was cooled down to 30-35° C. and filtered, the cake was washed with ethyl acetate (90 ml). The filtrate was heated to reflux temperature and 200 ml of solvent were distilled under atmospheric pressure and residual solution containing racemic voriconazole was obtained. This residual solution was cooled down to 20-25° C. and a thick suspension was then obtained. (1R)-(−)-10-camphorsulfonic acid (53.7 g, 0.231 mol) and methanol (1010 ml) were added. The mixture was heated to reflux temperature and 360-365 ml of solvent was distilled under atmospheric pressure. The resulting solution was cooled down to 21-22° C. and stirred for 2 hours. The suspension thus formed was filtered without washings, obtaining a wet off-white solid (41.49 g). The loss on drying at 50-60° C./vacuum gives a theoretical weight of 39.68 g and a yield of 59.0% calculated on the desired enantiomer.

The dried product corresponds to Voriconazole (1R)-(−)-10-camphorsulfonate Form B.

Analytical data of the dried product: HPLC enantiomeric purity (method A): 97.15%; HPLC chemical purity (method C): 99.96%; XRD (2θ): Form B, see FIG. 5; DSC (open pan): see FIG. 8; IR: see FIG. 6.

Example 2

Purification of Voriconazole

Voriconazole (20.5 g, enantiomeric purity 98.32%) was dissolved in isopropanol (51.3 ml) by heating. The solution was filtered at 65-70° C., cooled down to 0±1° C. and stirred for 1.5 hours. The suspension was filtered and the cake was washed with cold isopropanol (4 ml). A white solid was obtained after drying at 50-60° C. under vacuum until constant weight (18.43 g, 89.90% yield).

Figure 2:
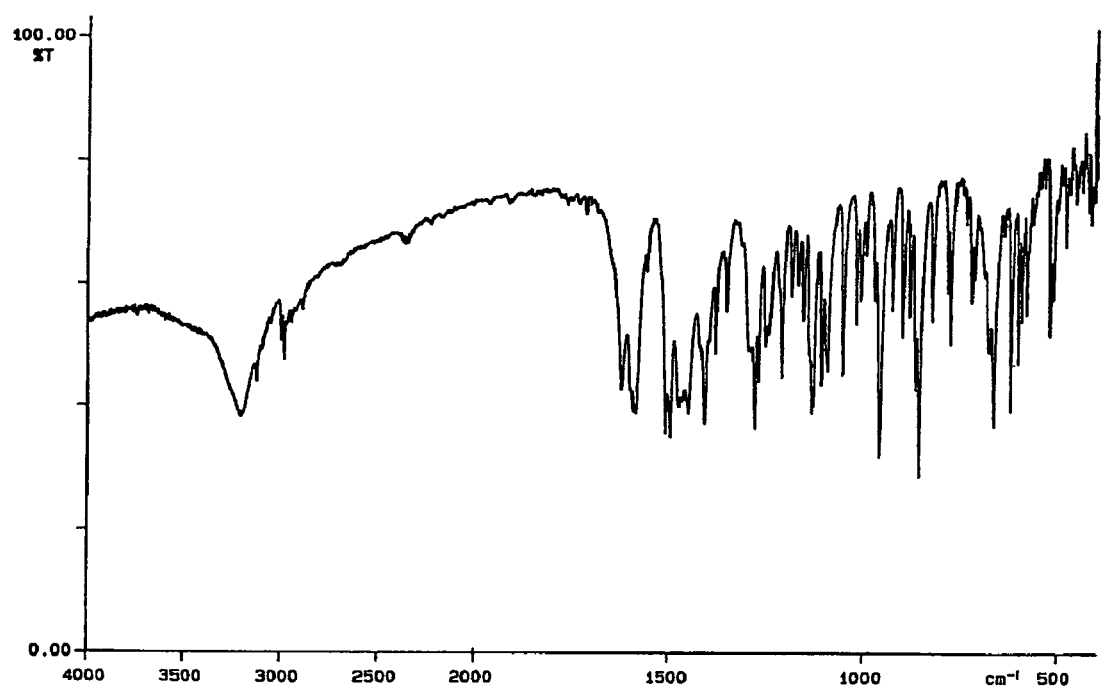
FIG. 2: illustrates the Infrared (IR) spectrum of Voriconazole Form I obtained in example 10

Analytical data: Enantiomeric purity (HPLC, method A): 99.92%, Chemical purity (HPLC, method C): 99.97%, XRD (2θ): form I, substantially identical to FIG. 1, IR: substantially identical to FIG. 2, Assay ($HClO_4$): 99.65%, Loss on drying: 0.13%, Water content: 0.08%, Residual isopropanol: 1284 ppm, Residual ethyl acetate: <100 ppm, Residue on ignition: <0.1%, Heavy metals: <10 ppm; Particle Size Distribution: D(v, 0.1): 36.9 µm, D(v, 0.5): 102.4 µm, D(v, 0.9): 220.0 µm

Example 3

Preparation of Racemic Voriconazole

Ethyl acetate (15 ml) was added to a mixture of (2R,3S/2S,3R)-3-(4-chloro-5-fluoropyrimidin-6-yl)-2-(2,4-difluorophenyl)-1-(1H-1,2,4-triazol-1-yl)butan-2-ol (5 g, 13.029 mmol), ammonium formate (1.64 g, 26.058 mmol) and 10% Pd/C wet (56.0%) catalyst (0.222 g). The suspension was heated to reflux temperature and stirred for 2 hours and 30 minutes. The reaction mixture was cooled down to 20-25° C., the solids were filtered and the cake was washed with ethyl acetate (2×25 ml). The filtrate was concentrated under vacuum until a residual volume of approximately 25 ml. The resulting solution was washed successively with aqueous saturated sodium bicarbonate solution (10 ml) and water (10 ml), filtered and concentrated under vacuum to dryness. Methanol (2.5 ml) was added and concentrated again under vacuum, obtaining a creamy solid (4.5 g, 99.0% yield).

Analytical data: Chemical purity (HPLC, method B): 97.66%.

Example 4

Preparation of Racemic Voriconazole

Ethyl acetate (15 ml) was added to a mixture of (2R,3S/2S,3R)-3-(4-chloro-5-fluoropyrimidin-6-yl)-2-(2,4-difluorophenyl)-1-(1H-1,2,4-triazol-1-yl)butan-2-ol (5 g, 13.029 mmol), ammonium formate (1.64 g, 26.058 mmol) and 10% Pd/C wet (56.0%) catalyst (0.222 g). The suspension was heated to reflux temperature and stirred for 2 hours and 30 minutes. The reaction mixture was cooled down to 20-25° C., solids were filtered and the cake was washed with ethyl acetate (4×25 ml). The filtrate was concentrated under vacuum to dryness. The residue was dissolved in ethyl acetate (9 ml) by heating at 55-60° C. The solution was cooled down to 20-25° C. and stirred for 1 hour and 30 minutes. The suspension was filtered and the cake was washed with cold ethyl acetate (2 ml). A white solid was obtained after drying under vacuum (2.75 g, 60% yield).

Analytical data: Chemical purity (HPLC, method B): 99.31%.

Example 5

Preparation of Racemic Voriconazole

Methanol (10 ml) was added to a mixture of (2R,3S/2S,3R)-3-(4-chloro-5-fluoropyrimidin-6-yl)-2-(2,4-difluorophenyl)-1-(1H-1,2,4-triazol-1-yl)butan-2-ol (1 g, 2.606 mmol), ammonium formate (0.328 g, 5.211 mmol) and 10% Pd/C wet (56.0%) catalyst (0.046 g). The suspension was heated to reflux temperature and stirred for 2 hours. The reaction mixture was cooled down to 20-25° C., the solids were filtered and the cake was washed with methanol (20 ml). The filtrate was concentrated under vacuum to dryness. The residue was dissolved in ethyl acetate (10 ml) and the resulting organic solution was washed with deionised water (4 ml), dried with anhydrous sodium sulphate and concentrated under vacuum to obtain quantitatively racemic Voriconazole.

Analytical data: Chemical purity (HPLC, method B): 96.40%.

Example 6

Preparation of Racemic Voriconazole

Sodium acetate (0.267 g, 3.257 mmol) was added to a solution of (2R,3S/2S,3R)-3-(4-chloro-5-fluoropyrimidin-6-yl)-2-(2,4-difluorophenyl)-1-(1H-1,2,4-triazol-1-yl)butan-2-ol (1 g, 2.606 mmol) in methanol (10 ml). After purging with argon, 10% Pd/C wet (56.0%) catalyst (0.083 g) was added and the mixture was hydrogenated at 20-25° C. under atmospheric pressure for 2 hours. The reaction mixture was filtered and the cake was washed with methanol (2×10 ml). The filtrate was concentrated under vacuum to dryness giving a crude residue (1.04 g) corresponding mainly to the product of the title.

Example 7

Preparation of Voriconazole (1R)-(−)-10-camphorsulfonate

A mixture of (2R,3S/2S,3R)-3-(4-chloro-5-fluoropyrimidin-6-yl)-2-(2,4-difluorophenyl)-1-(1H-1,2,4-triazol-1-yl)butan-2-ol (6 g, 15.6 mmol), ammonium formate (1.97 g, 31.2 mmol) and wet (54.9% moisture) 10% Pd/C catalyst (0.27 g) in ethyl acetate (18 ml) was heated to 60-65° C. and stirred at this temperature for 2 hours and 30 minutes. The mixture was cooled down to 30-35° C., filtered and the cake was washed with ethyl acetate (2×5 ml). 80% of the filtrate was distilled under reduced pressure until a doughy residue was obtained. Methanol (5 ml) was added and distillation continued.

One third of the residue was treated with (1R)-(−)-10-camphorsulfonic acid (0.97 g, 4.18 mmol) in methanol (14.6 ml) and the mixture was heated until complete solution, cooled down to 23-25° C. and stirred for 2 hours. The suspension thus formed was filtered and the obtained wet white solid was dried under vacuum at 50° C. to give Voriconazole (1R)-(−)-10-camphorsulfonate (0.71 g, 58% yield).

Analytical data: Enantiomeric purity (HPLC, method A): 93.87%, Chemical purity (HPLC, method C): 99.98%.

Example 8

Purification of Voriconazole (1R)-(−)-10-camphorsulfonate

Voriconazole (1R)-(−)-10-camphorsulfonate (2.2 g, enantiomeric purity 92.23%) was treated with methanol (7.7 ml) under reflux temperature for 5 minutes. The resulting mixture was cooled down to 0-5° C. and stirred for 1 hour. The suspension was filtered and the solid was dried under vacuum at 50-60° C. until constant weight. A white solid was obtained (1.83 g, 83.18% yield) corresponding to purified Voriconazole (1R)-(−)-10-camphorsulfonate.

Analytical data: Enantiomeric purity (HPLC, method A): 99.72%.

Example 9

Preparation of Voriconazole (1R)-(−)-10-camphorsulfonate Forms A and B

A mixture of racemic Voriconazole (5 g, 14.3 mmol) and (1R)-(−)-10-camphorsulfonic acid (3.33 g, 14.3 mmol) in methanol (50 ml) was heated until solution at 50-55° C. The solution was cooled down to 22-24° C., stirred for 2 hours and filtered. A white crystalline solid was isolated.

Figure 3:
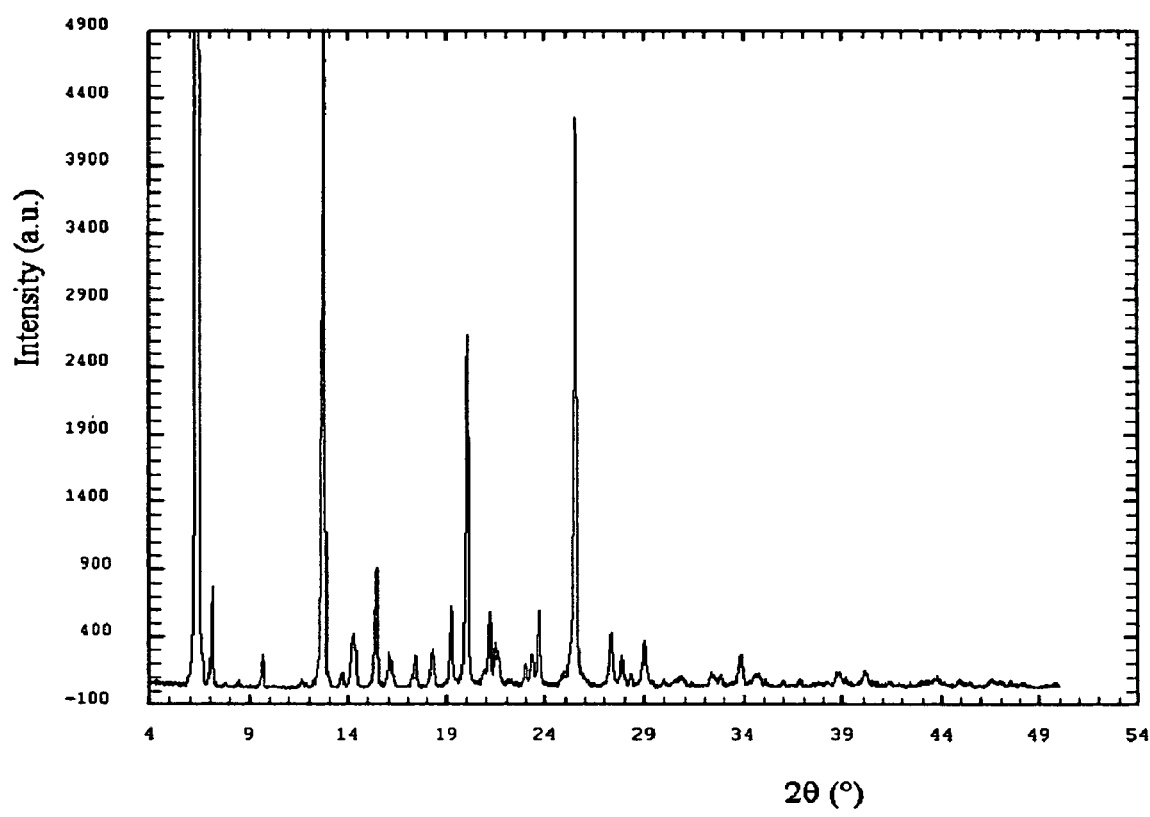
FIG. 3: illustrates the X-ray powder diffractogram (XRD) of Voriconazole (1R)-(−)-10-camphorsulfonate Form A obtained in example 9.
Figure 4:
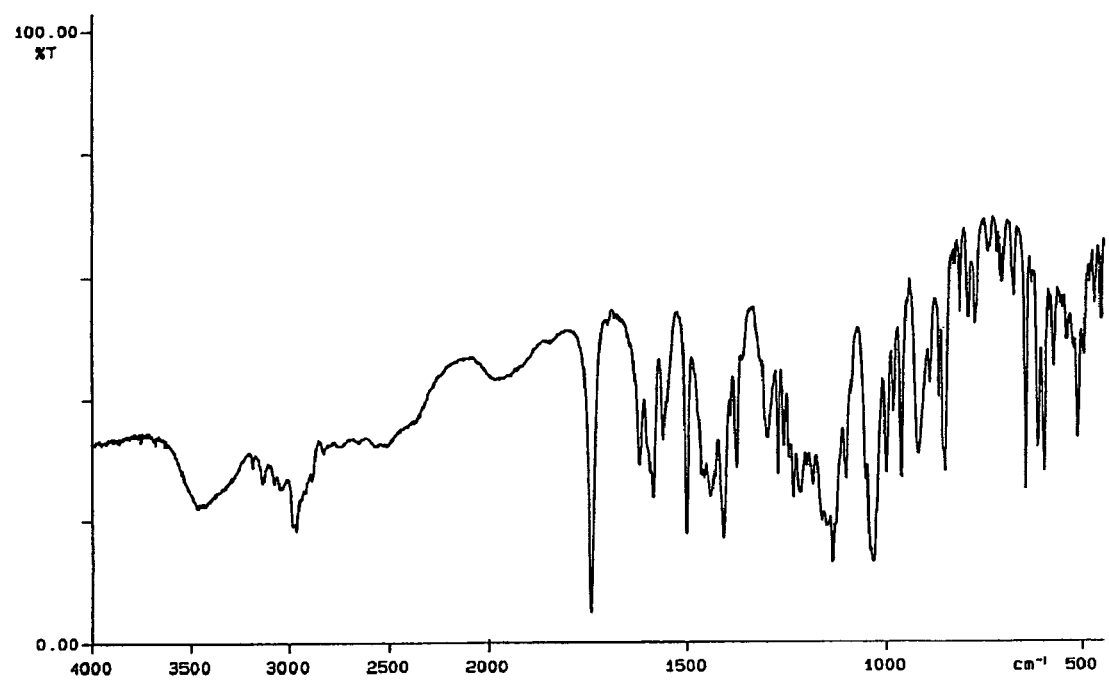
FIG. 4: illustrates the Infrared (IR) spectrum of Voriconazole (1R)-(−)-10-camphorsulfonate Form A obtained in example 9.

Analytical data: wet solid XRD (2θ): form A, see FIG. 3, IR: Form A, see FIG. 4 The wet solid was dried under vacuum at 55-60° C. until constant weight.

Analytical data: Chemical purity (HPLC, method C): 99.94%, XRD (2θ): Form B, substantially identical to FIG. 5.

Example 10

Preparation of Voriconazole Form I

The wet product obtained in Example 1 (Voriconazole (1R)-(−)-10-camphorsulfonate, 41.49 g wet, 40.36 g dry estimated, 0.069 mol) was suspended in ethyl acetate (121 ml) and aqueous saturated sodium bicarbonate solution (97 ml) was added slowly. The mixture was stirred for 10 minutes, the phases allowed to settle and the organic layer separated. The aqueous layer was re-extracted with ethyl acetate (91 ml). The combined organic layers were washed with deionised water (12 ml), filtered and concentrated under vacuum until a white doughy residue was obtained. Isopropanol (24 ml) was added and concentrated again under vacuum until a white doughy residue was obtained. Isopropanol (54.5 ml) was added and the suspension was heated until complete solution (60-65° C.). The solution was cooled down to 0-2° C. and stirred for at least 1 hour. The suspension formed was filtered, the cake was washed with cold isopropanol (6.1 ml). A white crystalline solid was obtained after drying at 55-60° C. under vacuum until constant weight: 19.75 g (81.43% yield).

Figure 9:
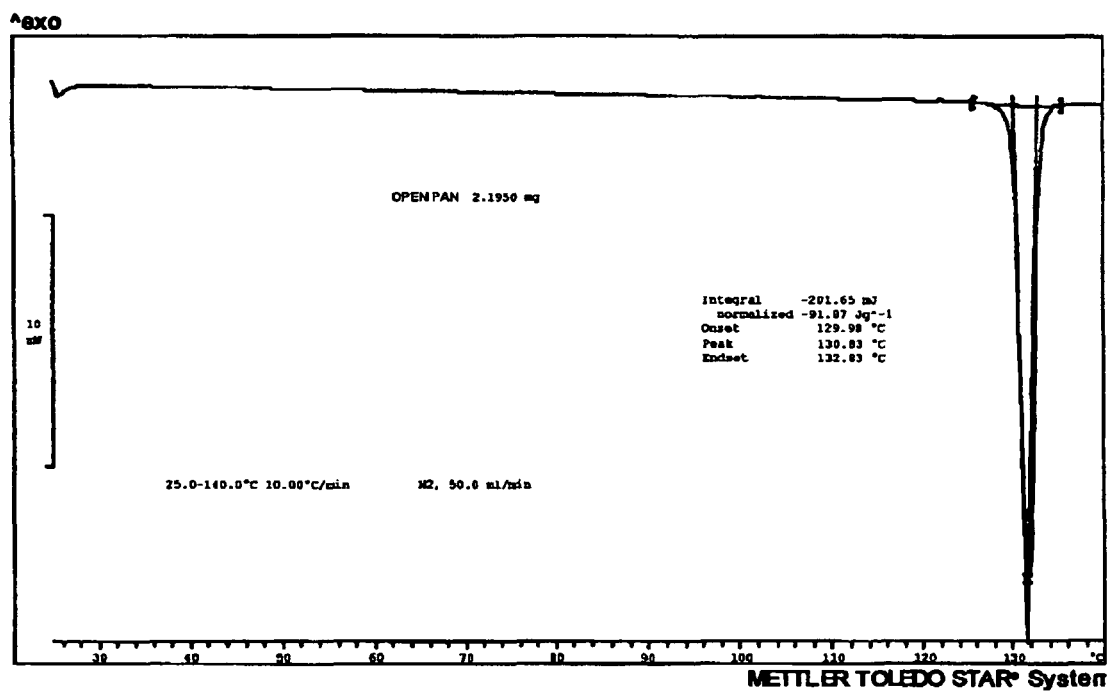
FIG. 9: illustrates the Differential Scanning Calorimetry (DSC) in an open pan of Voriconazole Form I obtained in example 10.

Analytical data: HPLC enantiomeric purity (HPLC, method A): 99.92%, Chemical purity (HPLC, method C): 100.0%, XRD (2θ): form I, see FIG. 1; IR: see FIG. 2; DSC (open pan): see FIG. 9; Assay (HClO$_4$): 99.30%, Loss on drying: 0.16%, Water content: 0.18%, Residual isopropanol: 209 ppm, Residual ethyl acetate: <100 ppm, Residue on ignition: <0.1%, Heavy metals: <10 ppm;

Example 11

Preparation of Voriconazole Form I

Voriconazole (1R)-(−)-10-camphorsulfonate (6 g, 10.3 mmol) was suspended in ethyl acetate (18 ml) and treated slowly with aqueous saturated solution of sodium bicarbonate (14.4 ml). The mixture was stirred for 10 minutes and allowed to settle. The organic phase was separated and the aqueous phase was re-extracted with ethyl acetate (13.5 ml). The combined organic phases were washed with deionised water (1.8 ml), filtered through paper and concentrated under reduced pressure to give a white solid (3.28 g, 91.11% yield).

Analytical data: Enantiomeric purity (HPLC, method A): 98.79%, Chemical purity (HPLC, method C): 99.99%, XRD (2θ): form 1, substantially identical to FIG. 1.

Example 12

Preparation of Voriconazole Form I

Voriconazole (1R)-(−)-10-camphorsulfonate (1 g, 1.72 mmol) was suspended in deionised water (10 ml) and treated with 5 N NaOH (0.34 ml, 1.72 mmol) at 45-55° C. for 2 hours and 30 minutes. The suspension was cooled down to 20-25° C., stirred for 15 minutes and filtered. The cake was washed with deionised water (15 ml). The solid was dried at 50-60° C. under vacuum until constant weight (0.523 g, 87.22% yield).

Analytical data: Enantiomeric purity (HPLC, method A): 97.65%, Chemical purity (HPLC, method C): 99.95%, XRD (2θ): form 1, substantially identical to FIG. 1.

Example 13

Preparation of Voriconazole

Voriconazole (1R)-(−)-10-camphorsulfonate (1 g, 1.72 mmol) was suspended in deionised water (10 ml) and treated with triethylamine (0.24 ml, 1.72 mmol) at 45-55° C. for 3 hours and 30 minutes. The suspension was cooled down to 20-25° C., stirred for 15 minutes and filtered. The cake was washed with deionised water (15 ml). The solid was dried under vacuum at 50-60° C. until constant weight (0.473 g, 78.78% yield).

Analytical data: Enantiomeric purity (HPLC, method A): 97.30%, Chemical purity (HPLC, method C): 99.94%.

Example 14

Preparation of Voriconazole

Voriconazole (1R)-(−)-10-camphorsulfonate (1 g, 1.72 mmol) was suspended in deionised water (10 ml) and treated with aqueous 10% w/v $Na_2CO_3$ (1.82 ml, 1.72 mmol) at 45-55° C. for 2 hours and 30 minutes. The suspension was cooled down to 20-25° C., stirred for 15 minutes and filtered. The cake was washed with deionised water (15 ml). The solid was dried at 50-60° C. under vacuum until constant weight (0.486 g, 81.07% yield).

Analytical data: Enantiomeric purity (HPLC, method A): 98.22%, Chemical purity (HPLC, method C): 99.94%.

Example 15

Preparation of Voriconazole (1R)-(−)-10-camphorsulfonate Form B

A mixture of racemic Voriconazole (70 g, 200.4 mmol) and (1R)-(−)-10-camphorsulfonic acid (46.55 g, 200.4 mmol) in methanol (700 ml) was heated until solution (45-50° C.). The solution was cooled down to 21-22° C., stirred for 2 hours and 15 minutes and filtered. The solid was dried under vacuum at 50° C. until constant weight to obtain a white crystalline solid. (34.45 g, 59.11% yield).

Analytical data: Enantiomeric purity (HPLC, method A): 98.62%, Chemical purity (HPLC, method C): 99.98%, XRD (2θ): Form B, substantially identical to FIG. 5, $[\alpha]_{25}=-53.9°$ (C=2, methanol), Residual methanol: 1.11%.

Example 16

Preparation of Voriconazole (1R)-(−)-10-camphorsulfonate

To a suspension of (2R,3S/2S,3R)-3-(4-chloro-5-fluoropyrimidin-6-yl)-2-(2,4-difluorophenyl)-1-(1H-1,2,4-triazol-1-yl)butan-2-ol hydrochloride (30 Kg, 71.39 mol) in ethyl acetate (73 Kg) was added slowly aqueous saturated sodium bicarbonate solution (63.4 Kg). The mixture was stirred for 30 minutes, the phases allowed to settle and the aqueous layer separated. The organic layer, which contained (2R,3S/2S,3R)-3-(4-chloro-5-fluoropyrimidin-6-yl)-2-(2,4-difluorophenyl)-1-(1H-1,2,4-triazol-1-yl)butan-2-ol as free base, was added to a mixture of ammonium formate (8.5 Kg, 134.79 mol) and wet (57.1% moisture) 10% Pd/C catalyst (1.20 Kg), heated to 60-65° C. and stirred at this temperature for 7 hours and 30 minutes. The mixture was cooled down to 30-35° C. and filtered, the cake was washed with ethyl acetate (24 Kg). Deionised water (12 Kg) was charged onto the filtrate, the mixture stirred for 30 minutes, the phases allowed to settle and the aqueous layer separated. The organic layer was heated to reflux temperature and 54 Kg of solvent were distilled under atmospheric pressure and residual solution containing racemic voriconazole was obtained. This residual solution was cooled down to 20-25° C. and a thick suspension was then obtained. A solution formed by (1R)-(−)-10-camphorsulfonic acid (16.1 Kg, 69.31 mol) and methanol (240 Kg) was added to the previous suspension. The mixture was heated to reflux temperature and 90 Kg of solvent were distilled under atmospheric pressure. The resulting solution was cooled down to 20-23° C. and stirred for 2 hours. The suspension thus formed was filtered washing the cake with methanol (5 Kg), obtaining a white solid (12.80 Kg).

Analytical data of a dried sample: HPLC enantiomeric purity (method A): 99.41%; HPLC chemical purity (method B): 99.97%; IR: substantially identical to FIG. 6.

Example 17

Purification of Voriconazole (1R)-(−)-10-camphorsulfonate

Voriconazole (1R)-(−)-10-camphorsulfonate (25.0 g, enantiomeric purity 98.69%) was dissolved with methanol (125 ml) under heating. The resulting solution was cooled down to 0-5° C. and stirred for 80 minutes. The suspension was filtered and the solid was dried under vacuum at 50-60° C. until constant weight. A white solid was obtained (22.14 g, 88.56% yield) corresponding to purified Voriconazole (1R)-(−)-10-camphorsulfonate.

Analytical data: Enantiomeric purity (HPLC, method A): 100.0%.

Example 18

Preparation of Voriconazole Form I

Voriconazole (1R)-(−)-10-camphorsulfonate (1 g, 1.72 mmol, enantiomeric purity 97.18%) was suspended in deionised water (10 ml) and treated with triethylamine (0.24 ml, 1.72 mmol) at 45-55° C. for 3 hours and 30 minutes. The suspension was cooled down to 20-25° C., stirred for 10 minutes and filtered. The cake was washed with deionised water (2×10 ml). The solid was dried under vacuum at 50-55° C. until constant weight (0.47 g, 78.26% yield).

Analytical data: Enantiomeric purity (HPLC, method A): 98.27%, Chemical purity (HPLC, method C): 100.0%, XRD (2θ): Form I, substantially identical to FIG. 1; Particle Size Distribution: D(v, 0.1): 4.5 μm, D(v, 0.5): 16.9 μm, D(v, 0.9): 37.4 μm, Mean Diameter: 18.7 μm.

Example 19

Preparation of Voriconazole Form I

Voriconazole (1R)-(−)-10-camphorsulfonate from example 12 (11 g, 18.9 mmol, enantiomeric purity 100.0%)

was suspended in deionised water (110 ml) and treated with triethylamine (2.90 ml, 20.8 mmol) at 45-55° C. for 3 hours. The suspension was cooled down to 20-25° C. and filtered. The cake was washed with deionised water (2×20 ml). The solid was dried under vacuum at 50-60° C. until constant weight (6.09 g, 92.13% yield).

Analytical data: Enantiomeric purity (HPLC, method A): 100.0%, Chemical purity (HPLC, method B): 99.98%, XRD (2θ): form I, substantially identical to FIG. 1, Assay (HClO$_4$): 101.05%, Loss on drying: 0.0%, Water content: 0.03%, Residual methanol: <100 ppm, Residue on ignition: <0.1%. Particle Size Distribution: D(v, 0.1): 5.7 μm, D(v, 0.5): 20.8 μm, D(v, 0.9): 43.4 μm, Mean Diameter: 23.3 μm.

Example 20

Preparation of Voriconazole Form I

Voriconazole (1R)-(−)-10-camphorsulfonate (1 g, 1.72 mmol, enantiomeric purity 97.18%) was suspended in deionised water (10 ml) and treated with aqueous 10% w/v Na$_2$CO$_3$ (1.82 ml, 1.72 mmol) at 45-55° C. for 2 hours and 30 minutes. The suspension was cooled down to 20-25° C., stirred for 10 minutes and filtered. The cake was washed with deionised water (2×10 ml). The solid was dried at 50-55° C. under vacuum until constant weight (0.48 g, 79.92% yield).

Analytical data: Enantiomeric purity (HPLC, method A): 98.42%, Chemical purity (HPLC, method C): 100.0%, XRD (2θ): Form I, substantially identical to FIG. 1; Particle Size Distribution: D(v, 0.1): 4.2 μm, D(v, 0.5): 14.9 μm, D(v, 0.9): 34.1 μm, Mean Diameter: 17.5 μm.

Example 21

Preparation of Voriconazole

Voriconazole (1R)-(−)-10-camphorsulfonate (4 g, 6.88 mmol, enantiomeric purity 98.52) was suspended in deionised water (40 ml) and treated with aqueous 10% w/v Na$_2$CO$_3$ (7.29 ml, 6.88 mmol) at 45-55° C. for 2 hours and 30 minutes. The suspension was cooled down to 20-25° C., stirred for 15 minutes and filtered. The cake was washed with deionised water (2×10 ml). The solid was dried at 50-60° C. under vacuum until constant weight (2.2 g, 91.67% yield).

Analytical data: Enantiomeric purity (HPLC, method A): 98.82%, Chemical purity (HPLC, method C): 100.0%, Assay (HClO$_4$): 99.57%; Particle Size Distribution: D(v, 0.1): 5.3 μm, D(v, 0.5): 16.7 μm, D(v, 0.9): 34.1 μm, Mean Diameter: 18.3 μm.

Example 22

Preparation of Voriconazole Form I

Voriconazole (1R)-(−)-10-camphorsulfonate from example 12 (11 g, 18.9 mmol, enantiomeric purity 100%) was suspended in deionised water (110 ml) and treated with aqueous 10% w/v Na$_2$CO$_3$ (20.4 ml, 18.9 mmol) at 45-55° C. for 2 hours and 30 minutes. The suspension was cooled down to 20-25° C. and filtered. The cake was washed with deionised water (2×20 ml). The solid was dried at 50-60° C. under vacuum until constant weight (6.18 g, 93.49% yield).

Analytical data: Enantiomeric purity (HPLC, method A): 100.0%, Chemical purity (HPLC, method B): 99.98%, XRD (2θ): form I, substantially identical to FIG. 1, IR: substantially identical to FIG. 2, Assay (HClO$_4$): 99.50%, Loss on drying: 0.12%, Water content: 0.04%, Residual methanol: <100 ppm, Residue on ignition: 0.10%; Particle Size Distribution: D(v, 0.1): 5.2 μm, D(v, 0.5): 19.1 μm, D(v, 0.9): 39.1 μm, Mean Diameter: 21.0 μm.

Example 23

Preparation of Voriconazole Form I

Voriconazole (1R)-(−)-10-camphorsulfonate (1.0 g, 1.72 mmol, enantiomeric purity 97.18%) was suspended in deionised water (50 ml) and treated with aqueous 10% w/v Na$_2$CO$_3$ (1.82 ml, 1.72 mmol) at 45-55° C. for 3 hours and 30 minutes. The suspension was cooled down to 20-25° C., stirred for 10 minutes and filtered. The cake was washed with deionised water (10 ml). The solid was dried at 50° C. under vacuum until constant weight (0.56 g, 93.24% yield).

Analytical data: Enantiomeric purity (HPLC, method A): 99.72%, Chemical purity (HPLC, method C): 100.0%, XRD (2θ): Form I, substantially identical to FIG. 1; Particle Size Distribution: D(v, 0.1): 5.2 μm, D(v, 0.5): 17.9 μm, D(v, 0.9): 37.5 μm, Mean Diameter: 19.8 μm.

Example 24

Preparation of Voriconazole Form I

The wet product obtained in Example 16 (Voriconazole (1R)-(−)-10-camphorsulfonate, 12.80 Kg wet, 12.59 Kg dry estimated, 22.01 mol) was suspended in ethyl acetate (33 Kg) and aqueous saturated sodium bicarbonate solution (30.60 Kg) was added slowly. The mixture was stirred for 30 minutes, the phases allowed to settle and the organic layer separated. The aqueous layer was re-extracted with ethyl acetate (25 Kg and 12 Kg). The combined organic layers were washed with deionised water (3.6 Kg), filtered washing the filter with ethyl acetate (9 Kg) and concentrated under vacuum until a white doughy residue was obtained. Isopropanol (5.6 Kg) was added and concentrated again under vacuum until a white doughy residue was obtained. Isopropanol (13.0 Kg) was added and the suspension was heated at reflux temperature until complete solution (83° C.). The solution was stirred at reflux temperature for 5 minutes, cooled down to 1±2° C. and stirred for at least 1 hour. The suspension formed was filtered, the cake was washed with cold isopropanol (2.0 Kg). A white crystalline solid was obtained after drying at 50-60° C. under vacuum until constant weight: 5.80 Kg. Weight after milling, sieving and blending: 5.70 Kg (22.8% yield from (2R,3S/2S,3R)-3-(4-chloro-5-fluoropyrimidin-6-yl)-2-(2,4-difluorophenyl)-1-(1H-1,2,4-triazol-1-yl)butan-2-ol hydrochloride).

Analytical data: HPLC enantiomeric purity (HPLC, method A): 99.98%; Chemical purity (HPLC, method D): 99.98%; XRD (2θ): form I, substantially identical to FIG. 1; IR: substantially identical to FIG. 2; Assay (HClO$_4$): 100.7%; Loss on drying: <0.05%; Water content: <0.05%; Residual isopropanol: 197 ppm; Residual ethyl acetate: <100 ppm; Residue on ignition: <0.05%; Heavy metals: <10 ppm; Particle Size Distribution: D(v, 0.1): 35.9 μm, D(v, 0.5): 147.6 μm, D(v, 0.9): 350.0 μm; Tapped Density: 0.82 g/ml; Foreign matter (as charcoal): <10 ppm; Palladium: 0.36 ppm.

Example 25

Preparation of Voriconazole

Voriconazole (1R)-(−)-10-camphorsulfonate (4 g, 6.88 mmol, enantiomeric purity 98.52) was suspended in deionised water (200 ml) and treated with aqueous 10% w/v Na$_2$CO$_3$ (7.29 ml, 6.88 mmol) at 45-55° C. for 3 hours and 30 minutes. The suspension was cooled down to 20-25° C., stirred for 15 minutes and filtered. The cake was washed with deionised water (2×10 ml). The solid was dried at 50-60° C. under vacuum until constant weight (2.07 g, 86.25% yield).

Analytical data: Enantiomeric purity (HPLC, method A): 99.77%, Chemical purity (HPLC, method C): 100.0%, Assay (HClO$_4$): 101.45%; Particle Size Distribution: D(v, 0.1): 5.4 µm, D(v, 0.5): 17.5 µm, D(v, 0.9): 37.2 µm, Mean Diameter: 19.4 µm.

Having thus described in detail preferred embodiments of the invention, it is to be understood that the invention defined by the appended claims is not to be limited to particular details set forth in the above description as many apparent variations thereof are possible without departing from the spirit or scope of the invention. Thus, it is intended that the present invention covers the modifications and variations of this invention that come within the scope of any claims and their equivalents.

What is claimed is:

1. A process for the preparation of Voriconazole which has an X-ray crystal diffraction pattern selected from the group consisting of:
   (a) a pattern with peaks at about 6.9°, 13.8°, 14.8°, 18.2°, 19.7°, 24.5°, 27.8° and 35.0°; and
   (b) a pattern with peaks at about 12.6°, 15.9°, 16.5°, 17.4°, 21.2°, 22.5°, 26.1°, 28.2° and 29.8°;
   by treating Voriconazole (1R)-(−)-10-camphorsulfonate with a non-chlorinated organic solvent and an aqueous alkaline solution, wherein the Voriconazole (1R)-(−)-10-camphorsulfonate is obtained by a process which comprises:
   (a) dehalogenation of

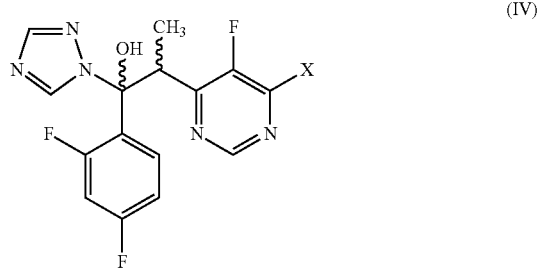

where X is a halogen,
   under catalytic transfer hydrogenation by using a catalyst in a solvent, wherein the obtained racemic Voriconazole is not isolated,
   (b) reacting the racemic Voriconazole with (1R)-(−)-10-camphorsulfonic acid in methanol,
   (c) optionally drying the obtained Voriconazole (1R)-(−)-10-camphorsulfonate.

2. The process of claim 1, wherein the dehalogenation is a dechlorination; X is chlorine and catalytic transfer hydrogenation is accomplished by using ammonium formate and Pd/C catalyst in a solvent selected from the group consisting of esters and alcohols.

3. The process of claim 2, wherein the solvent is ethyl acetate.

4. A process for the preparation of Voriconazole (1R)-(−)-10-camphorsulfonate wherein said compound has an X-ray powder diffraction pattern selected from the group consisting of:
   (a) a pattern with peaks at about 6.4°, 7.4°, 14.1°, 14.7°, 14.9°, 20.6°, 24.3° and 24.6° (2θ) (±0.2°);
   (b) a pattern with peaks at about 9.7°, 12.5°, 16.1°, 18.0°, 22.1°, 23.2°, 25.4° and 25.8° (2θ) (±0.2°); and
   (c) a pattern substantially identical to FIG. 5
   which comprises:
   (a) dehalogenation of

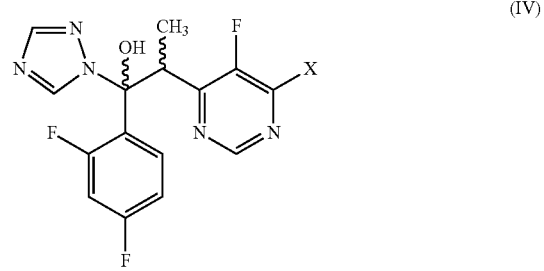

wherein X is halogen,
   under catalytic transfer hydrogenation by using a catalyst in a solvent, wherein the obtained racemic Voriconazole is not isolated,
   (b) reacting the racemic Voriconazole with (1R)-(−)-10-camphorsulfonic acid in methanol,
   (c) optionally drying the obtained Voriconazole (1R)-(−)-10-camphorsulfonate.

5. The process of claim 4, wherein the dehalogenation is a dechlorination; X is chlorine and catalytic transfer hydrogenation is accomplished by using ammonium formate and Pd/C catalyst in a solvent selected from the group consisting of esters and alcohols.

6. The process of claim 5, wherein the solvent is ethyl acetate.

7. Voriconazole (1R)-(−)-10-camphorsulfonate compound of Form B, wherein said compound has an X-ray powder diffraction pattern selected from the group consisting of:
   (a) a pattern with peaks at about 6.4°, 7.4°, 14.1°, 14.7°, 14.9°, 20.6°, 24.3° and 24.6° (2θ) (±0.2°);
   (b) a pattern with peaks at about 9.7°, 12.5°, 16.1°, 18.0°, 22.1°, 23.2°, 25.4° and 25.8° (2θ) (±0.2°); and
   (c) a pattern substantially identical to FIG. 5.

8. The compound of claim 7, wherein said compound has an enantiomeric purity selected from the range consisting of >95% and between about 96.50% and about 99.50% and has a chemical purity of >99.00% and between about 99.00% and about 100.00%.

9. Voriconazole obtained by the process of claim 1 which has an X-ray crystal diffraction pattern selected from the group consisting of:
   (a) a pattern with peaks at about 6.9°, 13.8°, 14.8°, 18.2°, 19.7°, 24.5°, 27.8° and 35.0°; and
   (b) a pattern with peaks at about 12.6°, 15.9°, 16.5°, 17.4°, 21.2°, 22.5°, 26.1°, 28.2° and 29.8°.

10. A process for making Voriconazole which has an X-ray crystal diffraction pattern selected from the group consisting of:
   (a) a pattern with peaks at about 6.9°, 13.8°, 14.8°, 18.2°, 19.7°, 24.5°, 27.8° and 35.0°; and
   (b) a pattern with peaks at about 12.6°, 15.9°, 16.5°, 17.4°, 21.2°, 22.5°, 26.1°, 28.2° and 29.8°;
   which comprises treating Voriconazole (1R)-(−)-10-camphorsulfonate of Form B of claim 7 with a non-chlorinated organic solvent and an aqueous alkaline solution.

11. The process of claim 2, wherein the esters and alcohols are $C_3$-$C_6$ esters and $C_1$-$C_6$ alcohols.

12. The process of claim 2, wherein $C_3$-$C_6$ esters and $C_1$-$C_6$ alcohols are ethyl acetate and methanol.

13. The process of claim 5, wherein the esters and alcohols are $C_3$-$C_6$ esters and $C_1$-$C_6$ alcohols.

14. The process of claim 5, wherein $C_3$-$C_6$ esters and $C_1$-$C_6$ alcohols are ethyl acetate and methanol.

* * * * *